US010881673B2

(12) United States Patent
Kwak et al.

(10) Patent No.: US 10,881,673 B2
(45) Date of Patent: Jan. 5, 2021

(54) CONJUGATE INCLUDING CORE AND SIALIC ACID OR DERIVATIVE THEREOF BOUND TO SURFACE OF CORE AND USE THEREOF

(71) Applicants: Kabio R&D SOO Co., Ltd., Seoul (KR); Rensselaer Polytechnic Institute, Troy, NY (US)

(72) Inventors: Jong Hwan Kwak, Gyeonggi-do (KR); Seok-Joon Kwon, Niskayuna, NY (US); Robert J. Linhardt, Albany, NY (US); Jonathan S. Dordick, Schenectady, NY (US); Fuming Zhang, Watervliet, NY (US)

(73) Assignees: Kabio R&D SOO Co., Ltd., Seoul (KR); Rensselaer Polytechnic Institute, Troy, NY (US)

( * ) Notice: Subject to any disclaimer, the term of this patent is extended or adjusted under 35 U.S.C. 154(b) by 0 days.

(21) Appl. No.: 15/679,709

(22) Filed: Aug. 17, 2017

(65) Prior Publication Data
US 2018/0050056 A1    Feb. 22, 2018

Related U.S. Application Data

(60) Provisional application No. 62/376,666, filed on Aug. 18, 2016.

(51) Int. Cl.
| A61K 31/7016 | (2006.01) |
| A61K 47/59 | (2017.01) |
| A61K 47/69 | (2017.01) |

(52) U.S. Cl.
CPC ........ *A61K 31/7016* (2013.01); *A61K 47/595* (2017.08); *A61K 47/6935* (2017.08)

(58) Field of Classification Search
CPC .............. A61K 31/7016; A61K 47/595; A61K 47/6935
See application file for complete search history.

(56) References Cited

FOREIGN PATENT DOCUMENTS

| KR | 10-2011-0096940 | 8/2011 |
| KR | 10-2011-0127034 | 11/2011 |

OTHER PUBLICATIONS

Jeffrey Landers, et al, Prevention of Influenza Pneumonitis by Sialic Acid-Conjugated Dendritic Polymers, 186 J Infect. Dis. 1222 (Year: 2002).*
A.S. Gambaryan, et al, Spec. of Receptor-Binding Phenotypes of Influenza Virus Isolates from Different Hosts Using Synth. Sialylglycopolymers: Non-Egg-Adapted Human H1 and H3 Influenza a and Influenza B Viruses Share a Common High Binding Affinity for 6'Sialyl(N-acetyllactosamine), 232 Virology 345 (Year: 1997).*
Irina Carlescu, et al, Synthetic Sialic Acid-Containing Polyvalent Antiviral Inhibitors, 19 Med. Chem. Res. 477 (Year: 209).*
Borges et al "Multivalent Dendrimeric Compounds Containing Carbohydrates Expressed on Immune Cells Inhibit Infection by Primary Isolates of HIV-1" Virology vol. 408, pp. 80-88, 2010.
Hendricks et al "Sialylneolacto-N-Tetraose C (LSTc)-Bearing Liposomal Decoys Capture Influenza a Virus" The Journal of Biological Chemistry vol. 288, pp. 8061-8073, 2013.
Kwon et al "Nanostructured Glycan Architecture is Important in the Inhibition of Influenza a Virus Infection" Nature Nanotechnology vol. 12, pp. 48-56, 2017.
Matsuoka et al "An Alternative Route for the Construction of Carbosilane Dendrimers Uniformly Functionalized with Lactose or Sialyllactose Moieties" Tetrahedron Letters vol. 42, pp. 3327-3330, 2001.
Oka et al "Syntheses and Biological Evaluations of Carbosilane Dendrimers Uniformly Functionalized with Sialyl a(243) Lactose Moieties as Inhibitors for Human Influenza Viruses" Bioorganic and Medicinal Chemistry vol. 17, pp. 5465-5475, 2009.
Papp et al "Inhibition of Influenza Virus Activity by Multivalent Glycoarchitectures with Matched Sizes" ChemBioChem vol. 12, pp. 887-895, 2011.
Papp et al "Inhibition of Influenza Virus Infection by Multivalent Sialic-Acid-Functionalized Gold Nanoparticles" Small vol. 6, pp. 2900-2906, 2010.
Tsvetkov et al "Neoglycoconjugates Based on Dendrimer Poly(Aminoamides)" Russian Journal of Bioorganic Chemistry vol. 28, pp. 470-486, 2002.

* cited by examiner

*Primary Examiner* — Sean M Basquill
(74) *Attorney, Agent, or Firm* — Cesari & McKenna, LLP

(57) ABSTRACT

Provided are a conjugate including a core and sialic acids or derivatives thereof bound to the surface of the core, and use thereof. The conjugate provided in the present invention binds with hemagglutinin on the surface of influenza virus to inhibit the course of infection of influenza virus, thereby preventing or treating infection of influenza virus and also preventing or treating infection of influenza virus resistant to antiviral agents. Accordingly, the conjugate may be widely used in the development of prophylactic or therapeutic agents for influenza virus infection.

15 Claims, 18 Drawing Sheets

[FIG. 1A]
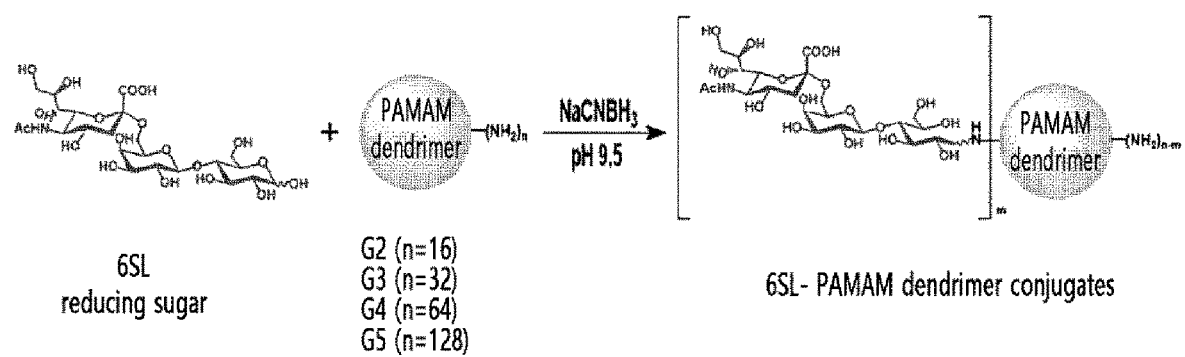

[FIG. 1B]
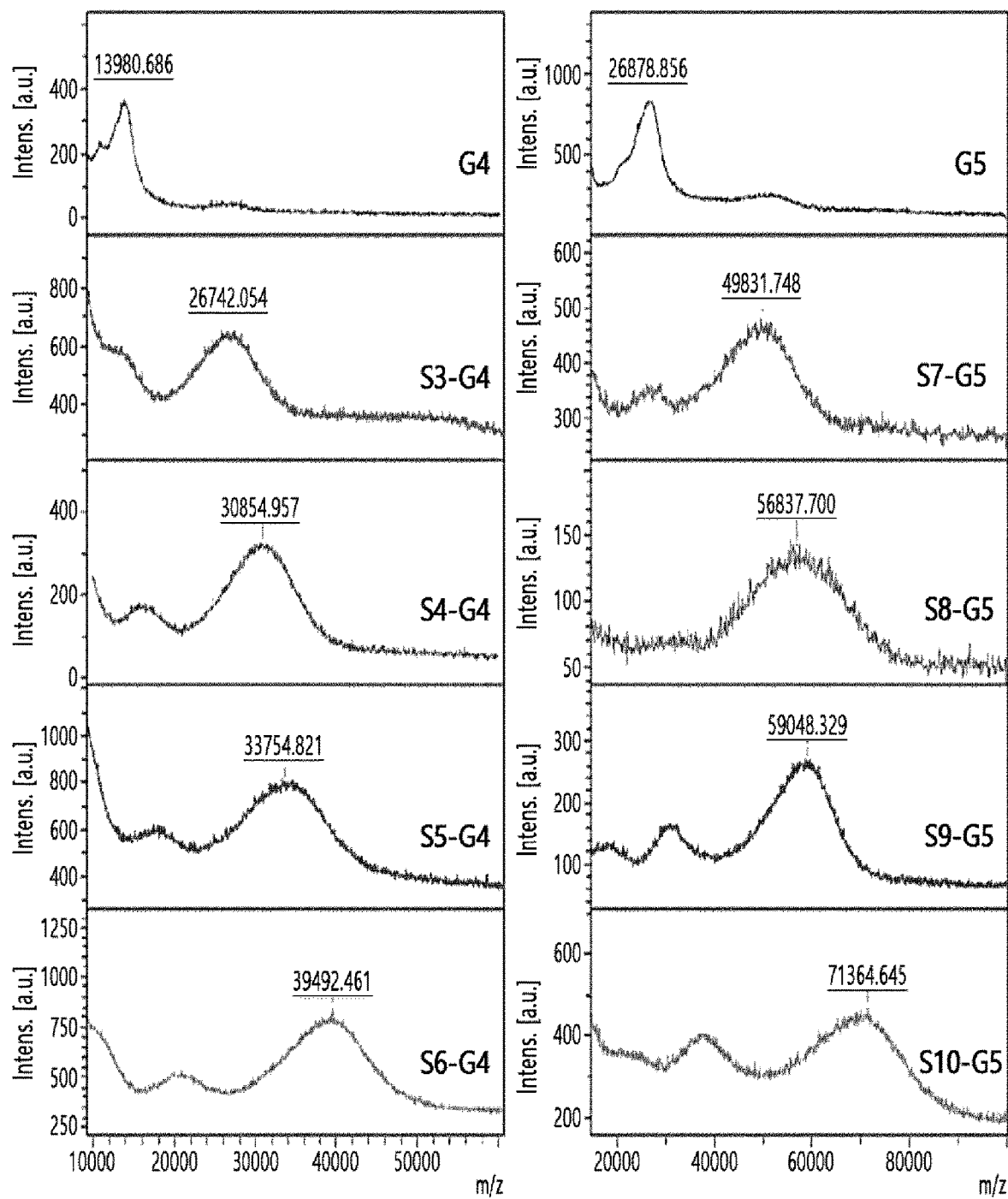

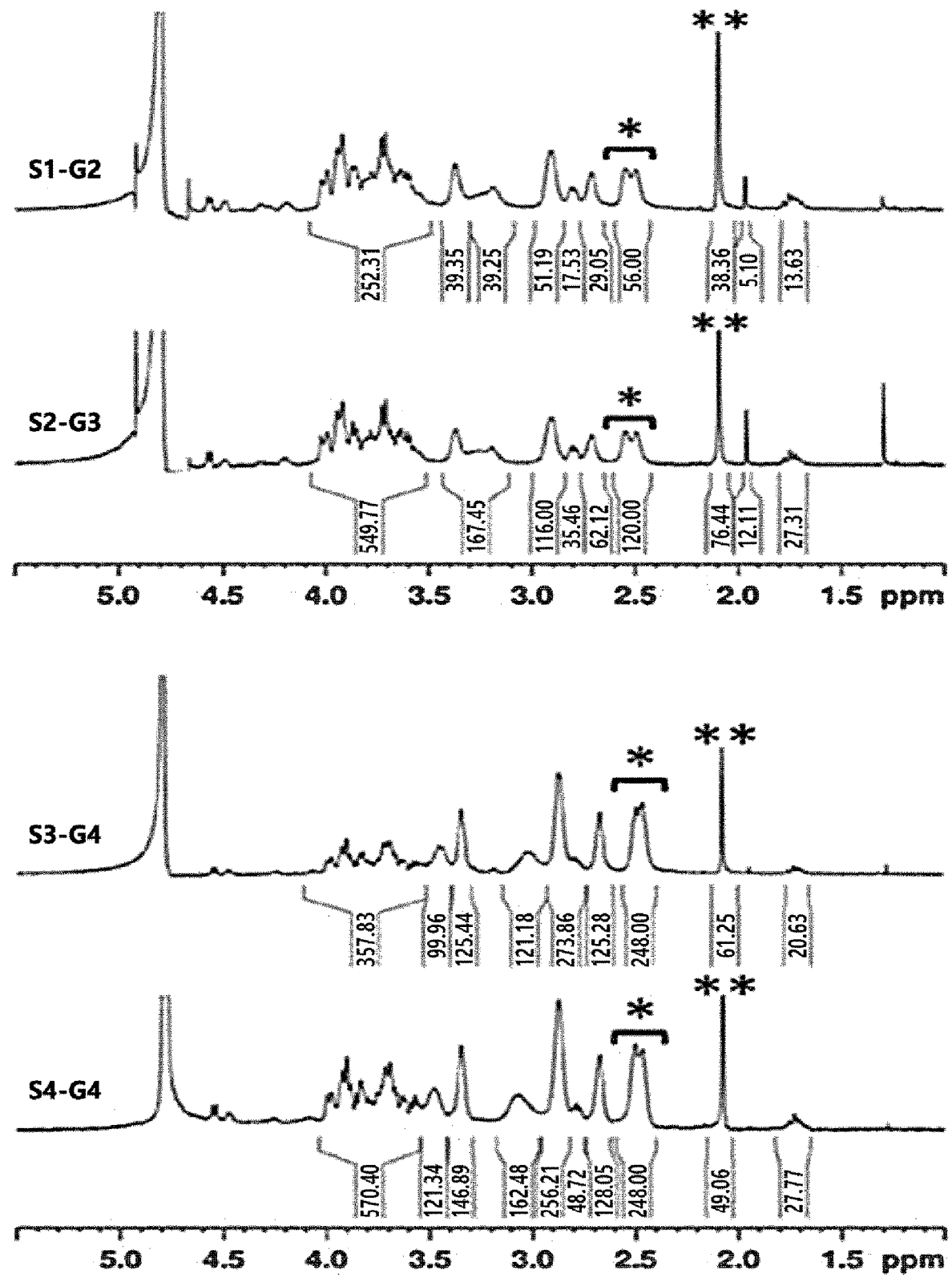
[FIG. 1C]

[FIG. 1D]
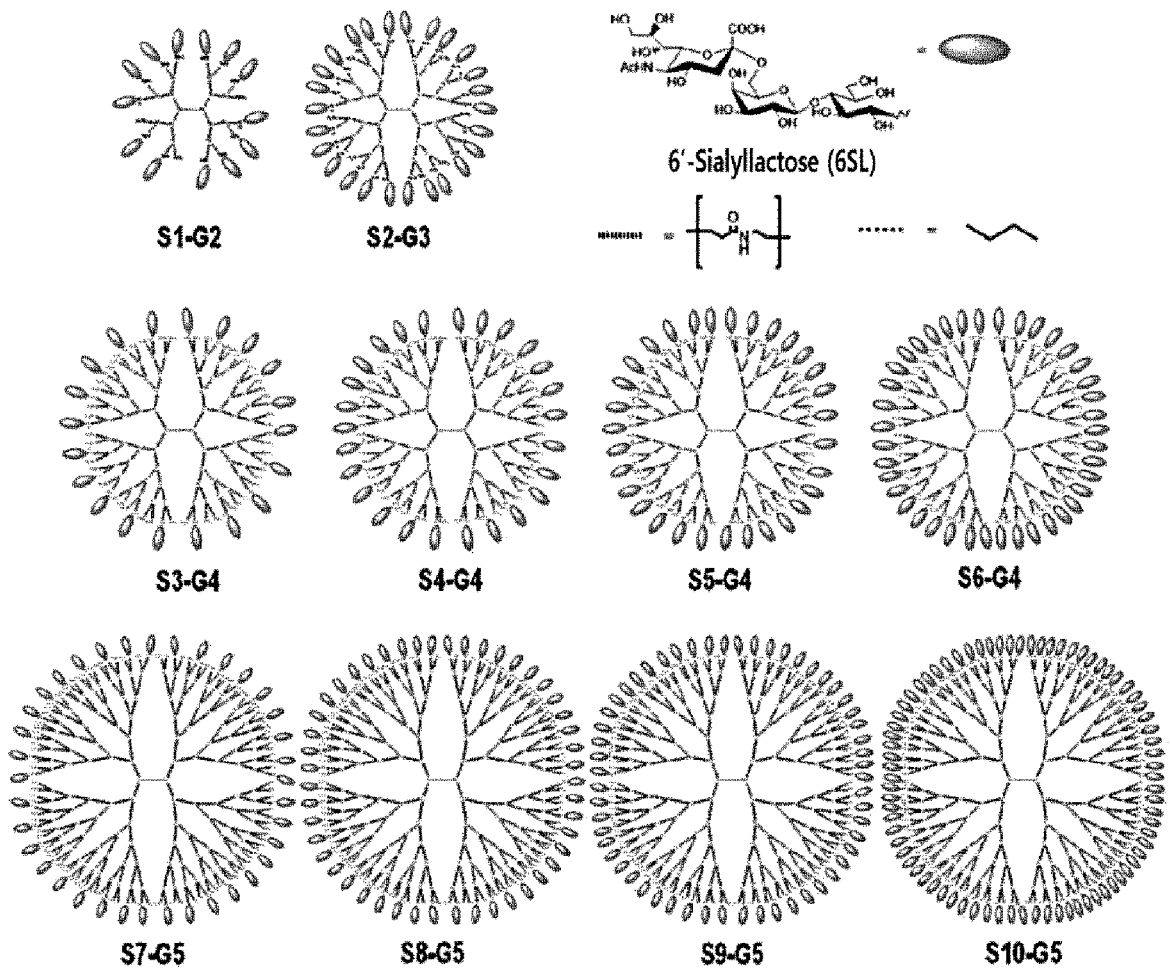

[FIG. 1E]
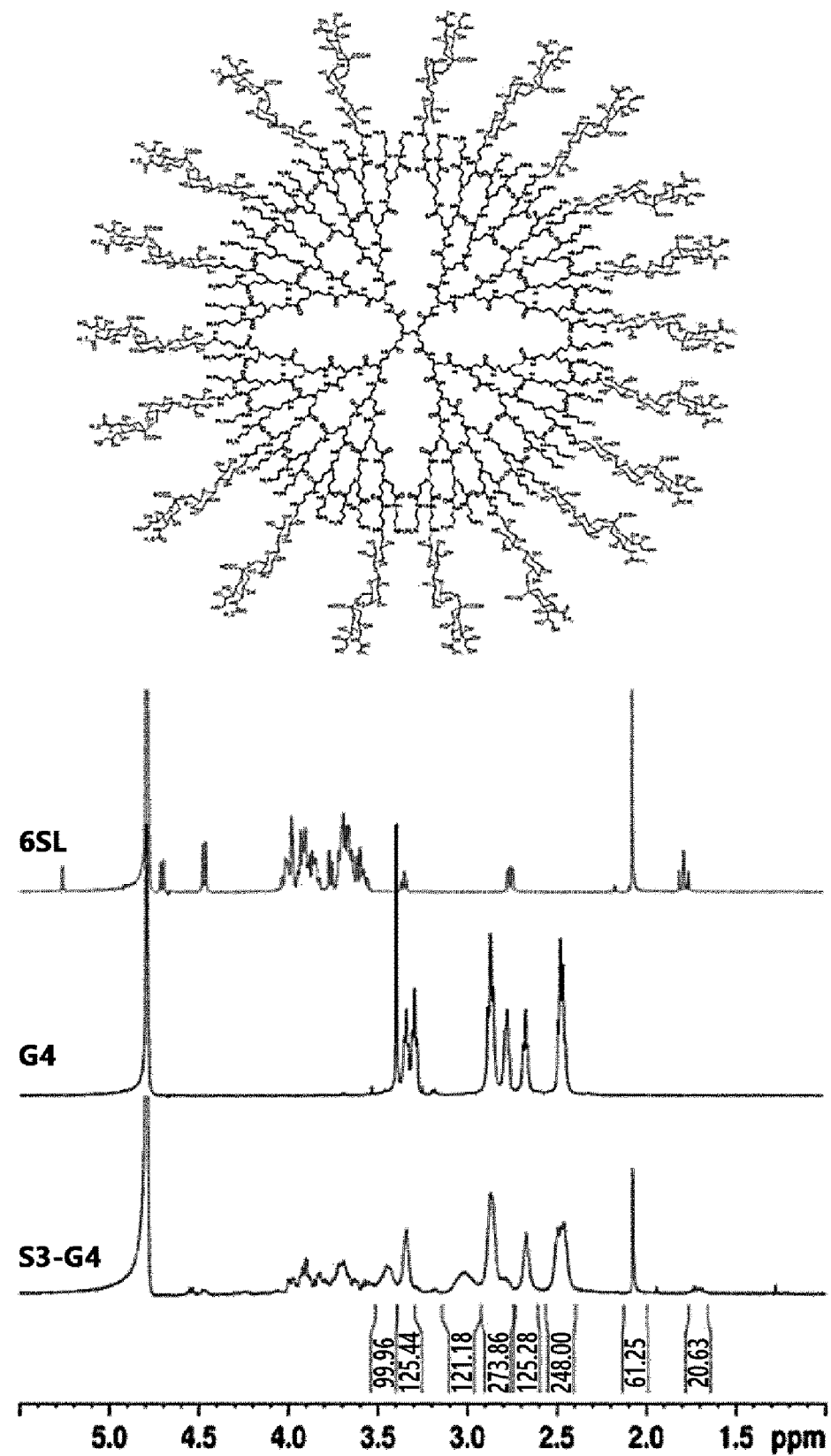

[FIG. 2A]
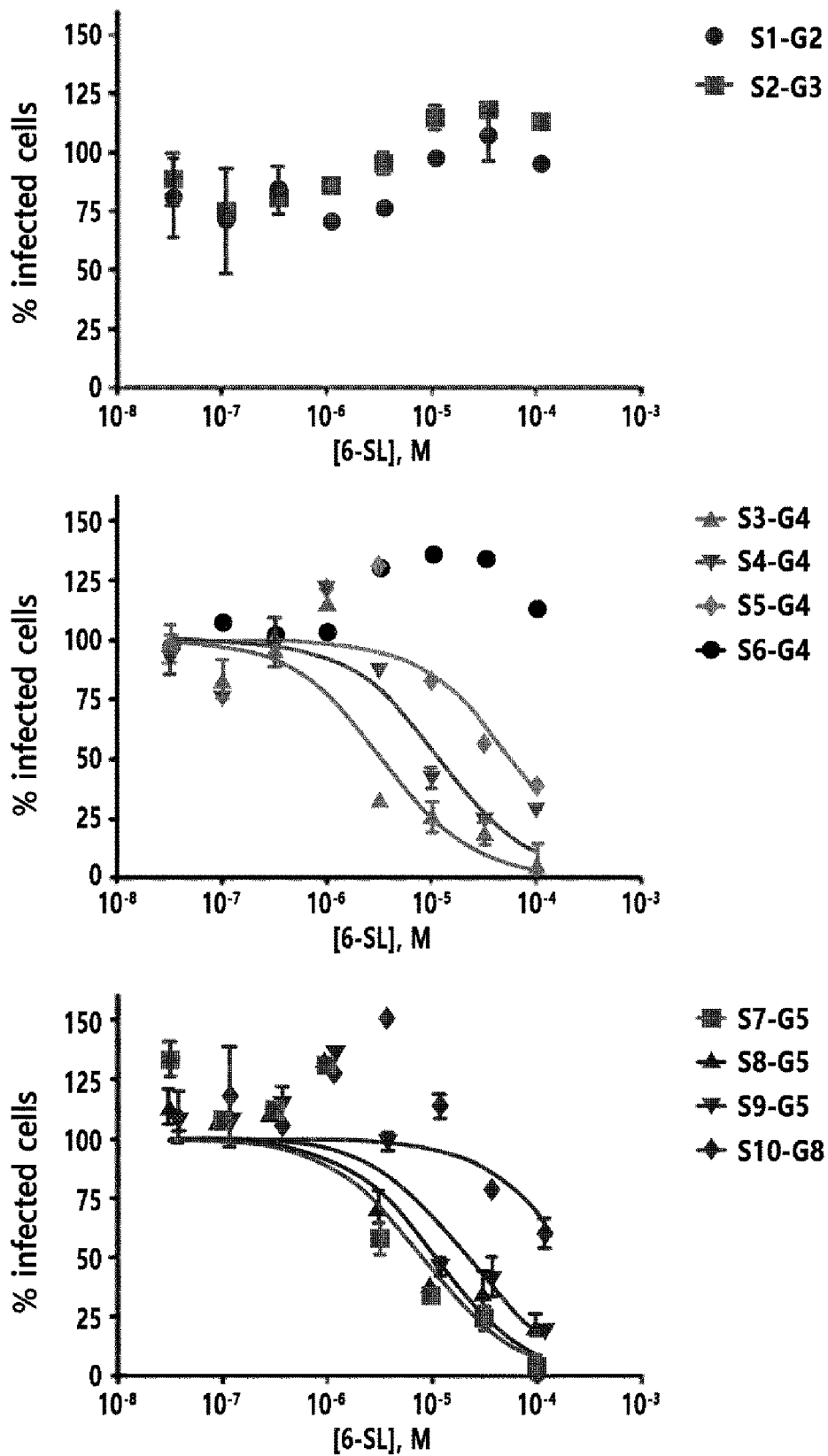

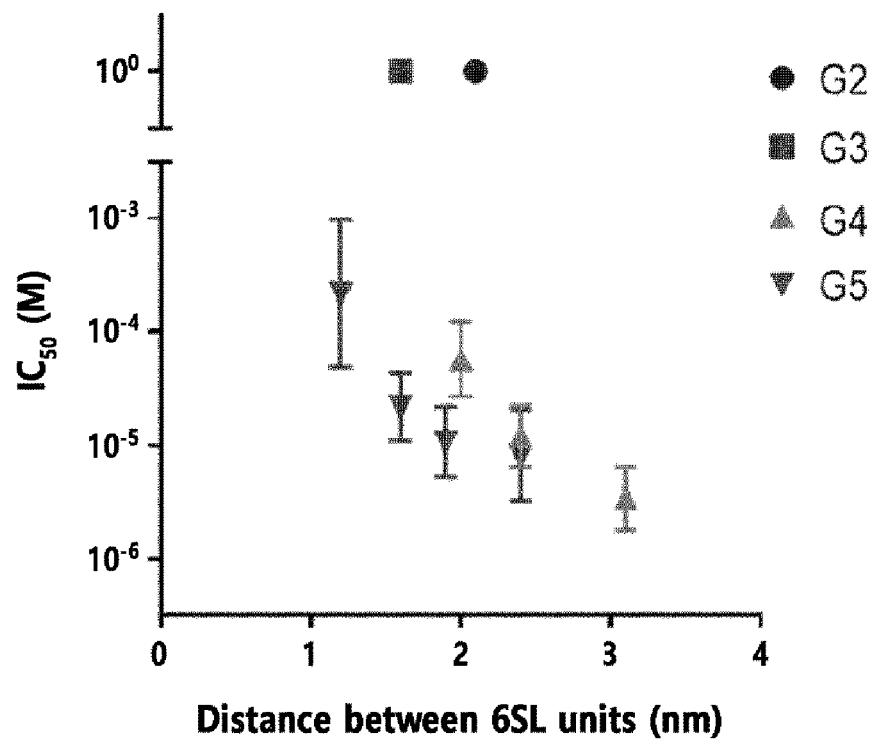
[FIG. 2B]

[FIG. 3A]
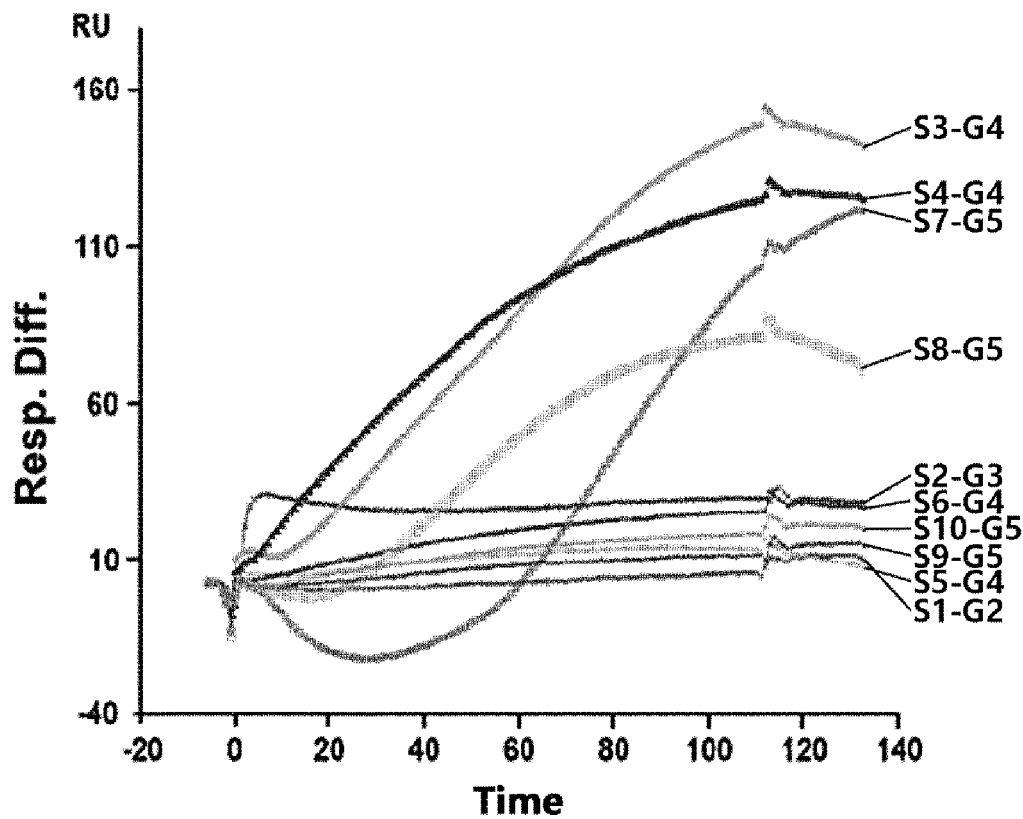
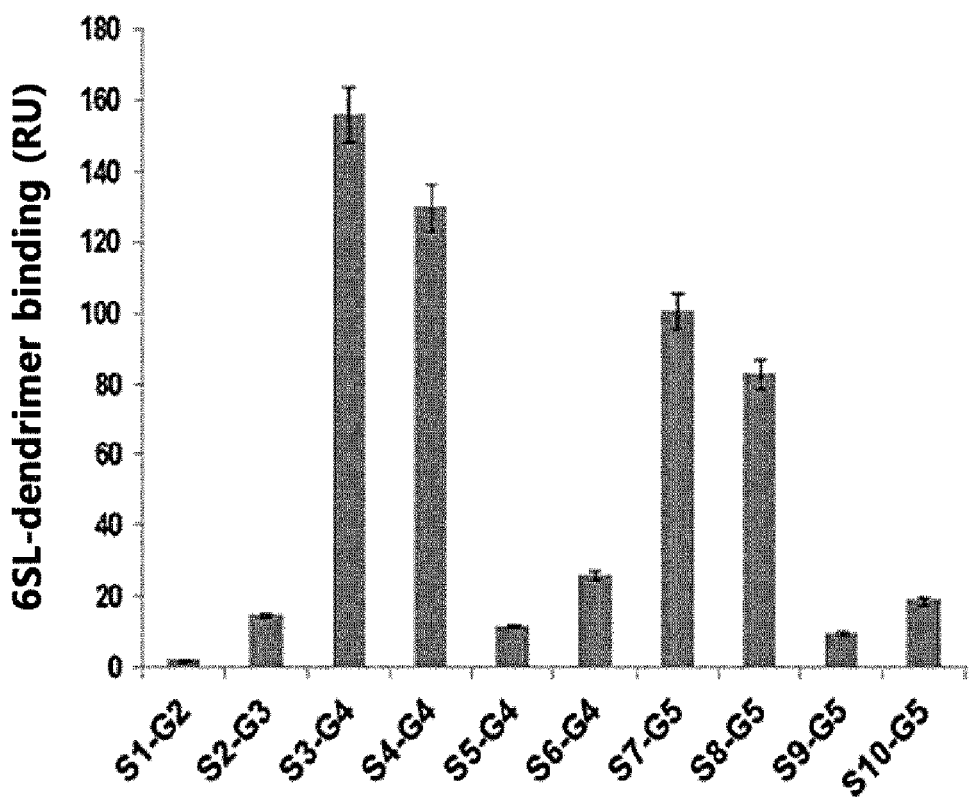

[FIG. 3B]

[FIG. 3C]
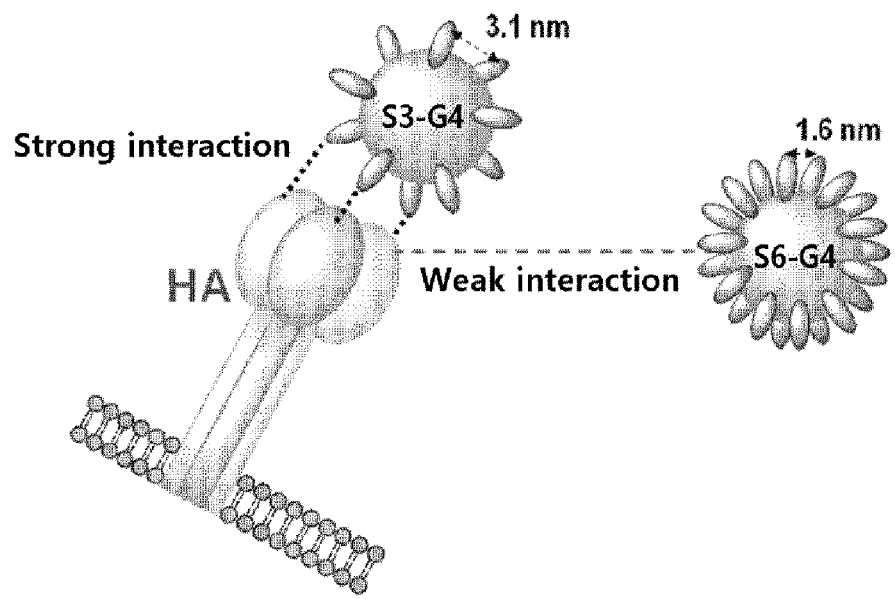

[FIG. 4]

[FIG. 5]
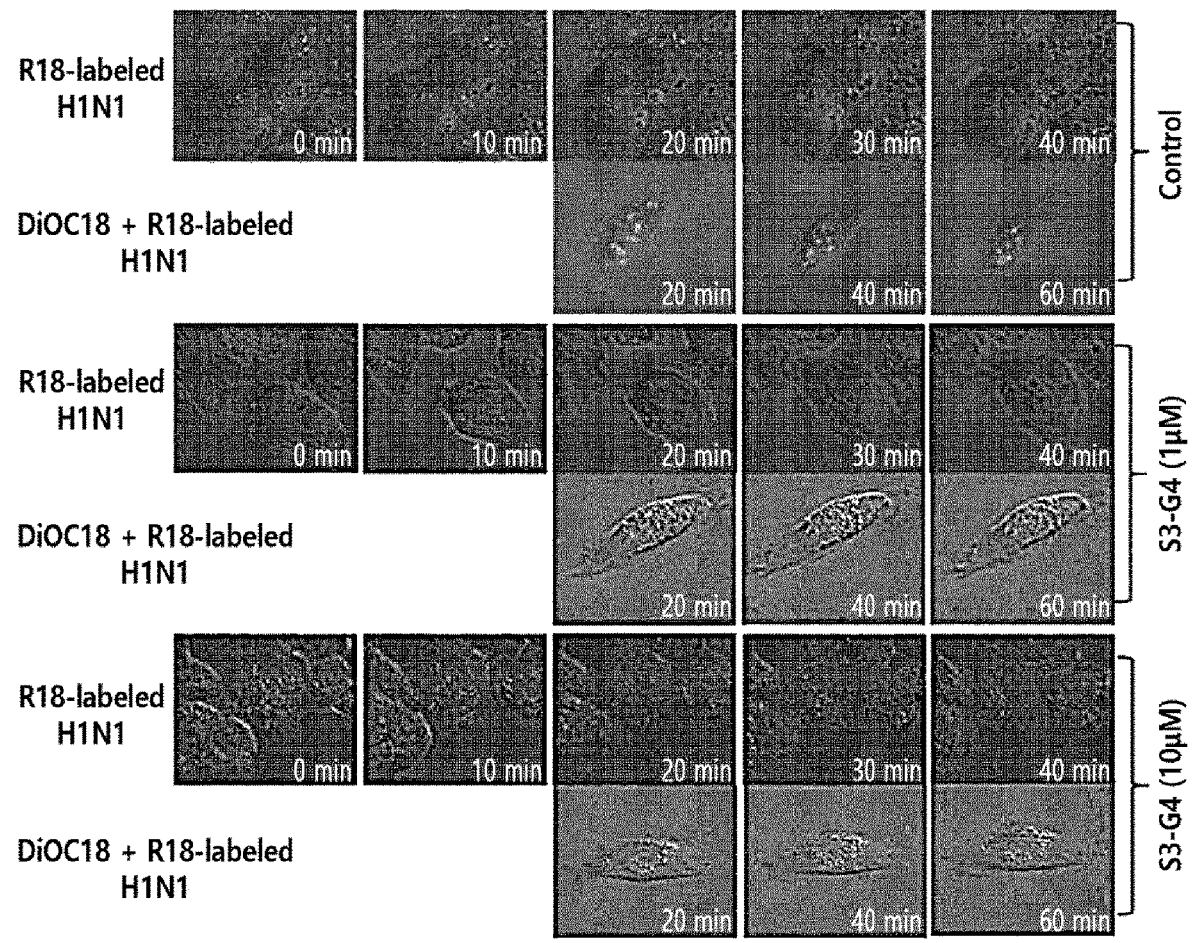

[FIG. 6]
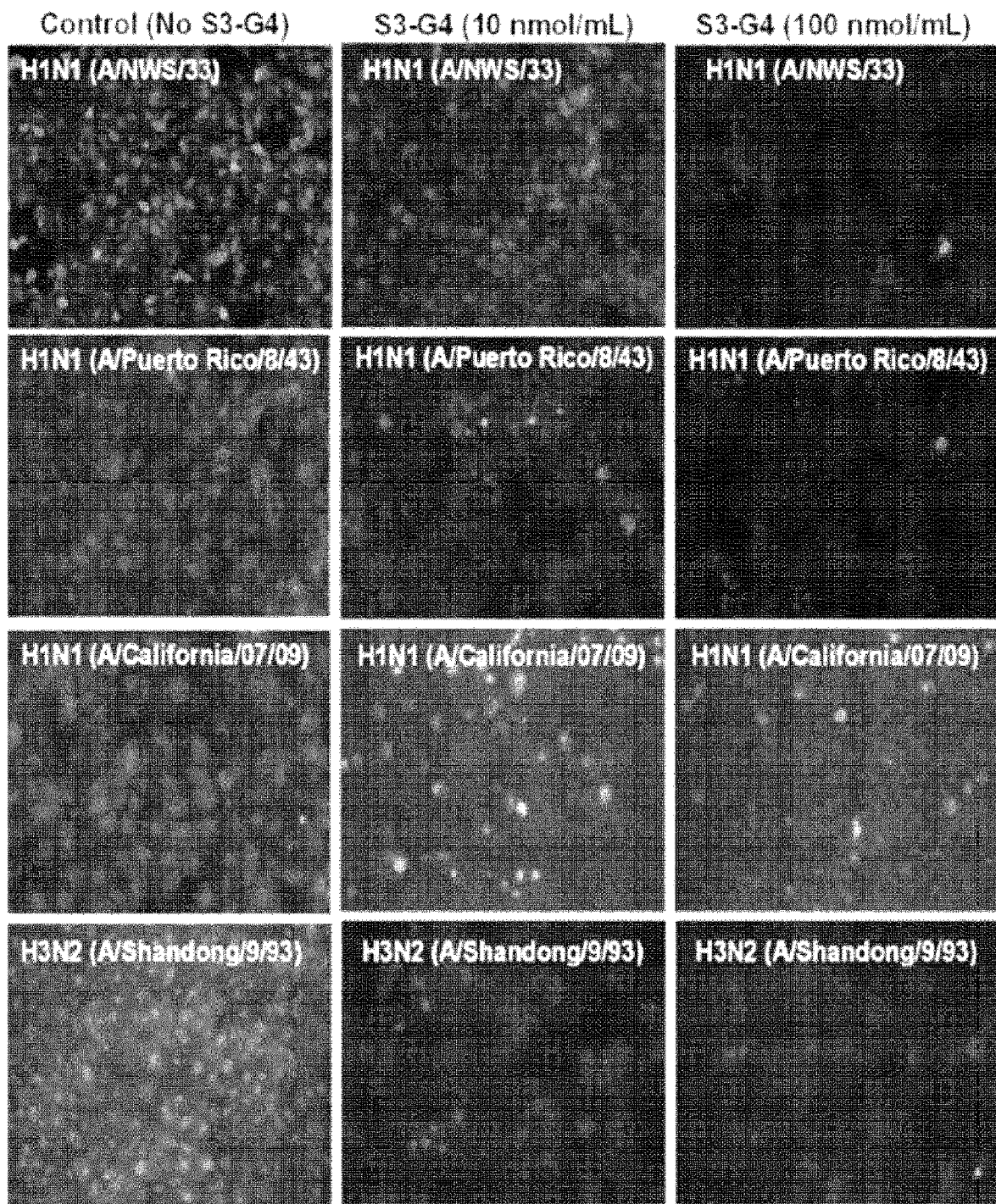

[FIG. 7A]

Virus titer

H1N1     H1N1 + S3-G4

(y-axis: $\log TCID_{50}/mL$)

[FIG. 7C]
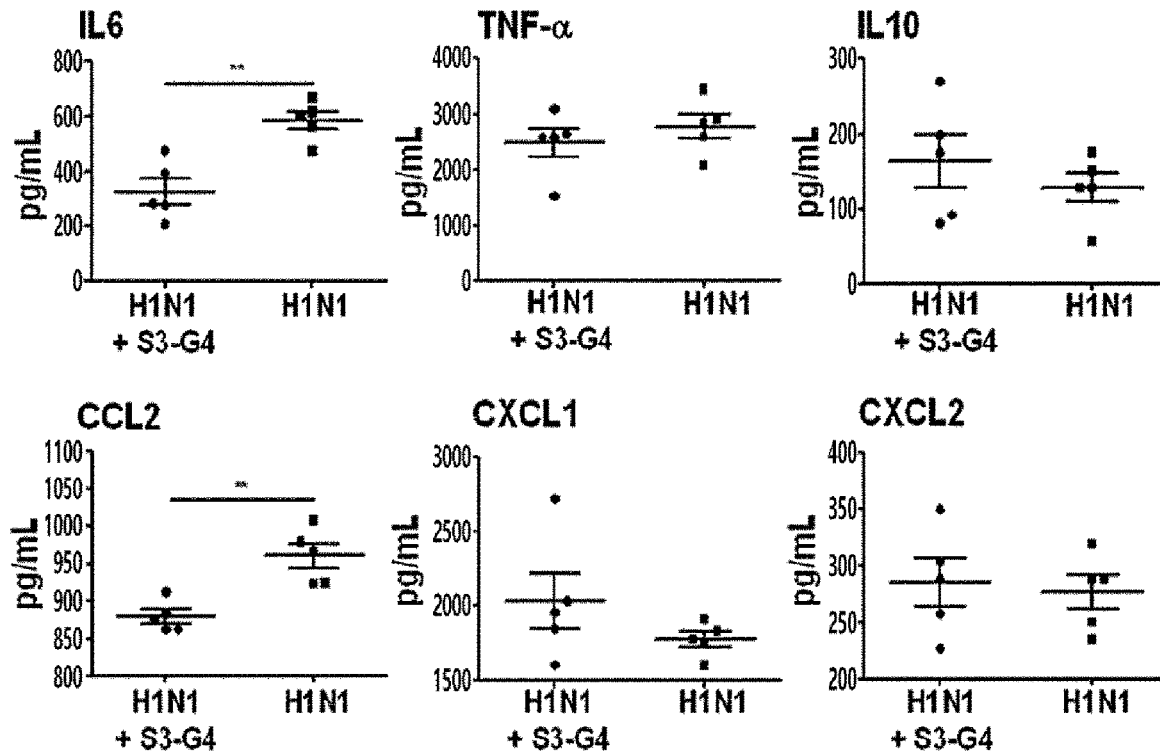
[FIG. 7D]
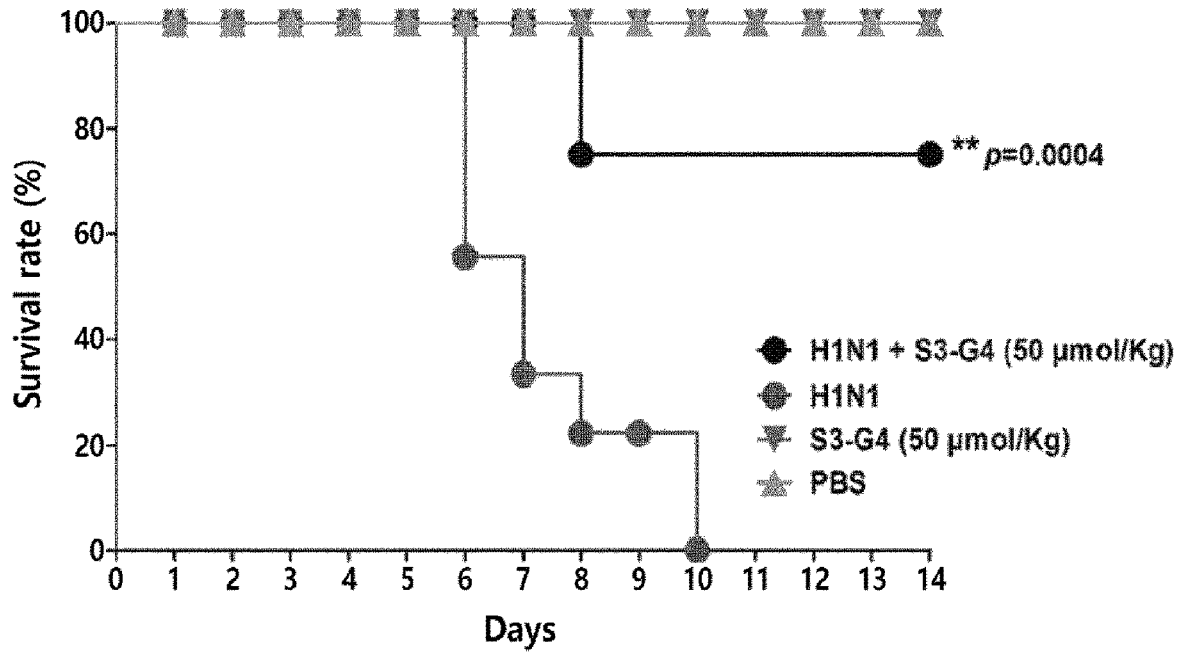

[FIG. 7E]
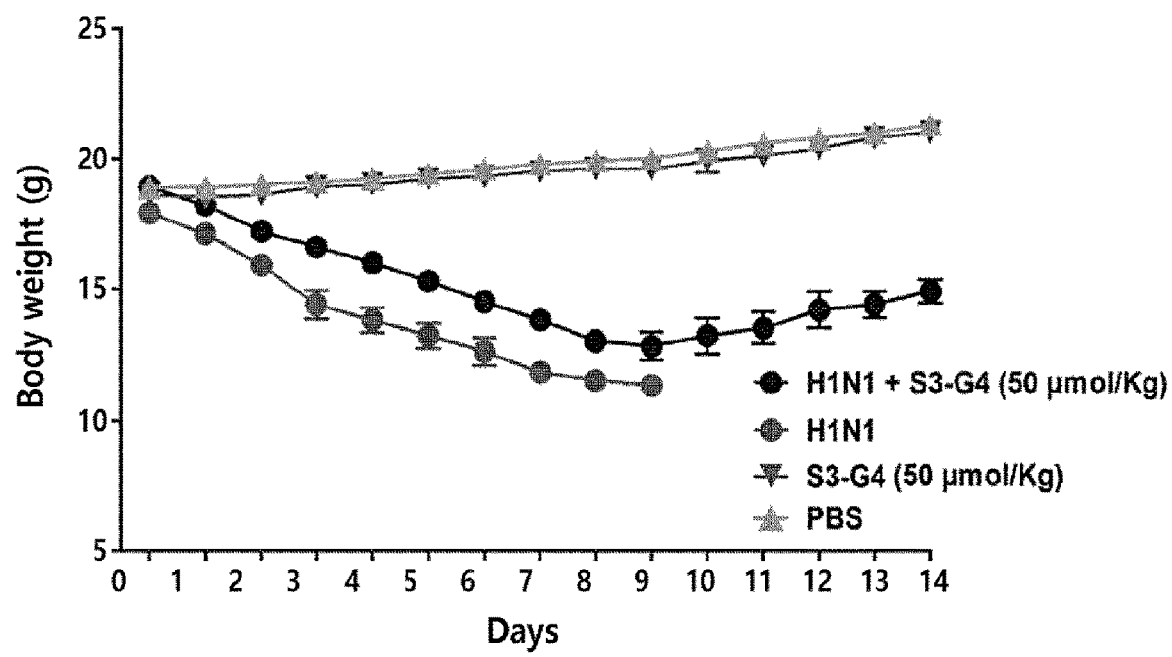
[FIG. 8A]
H1N1 (A/Gyeongnam/1820/2009)
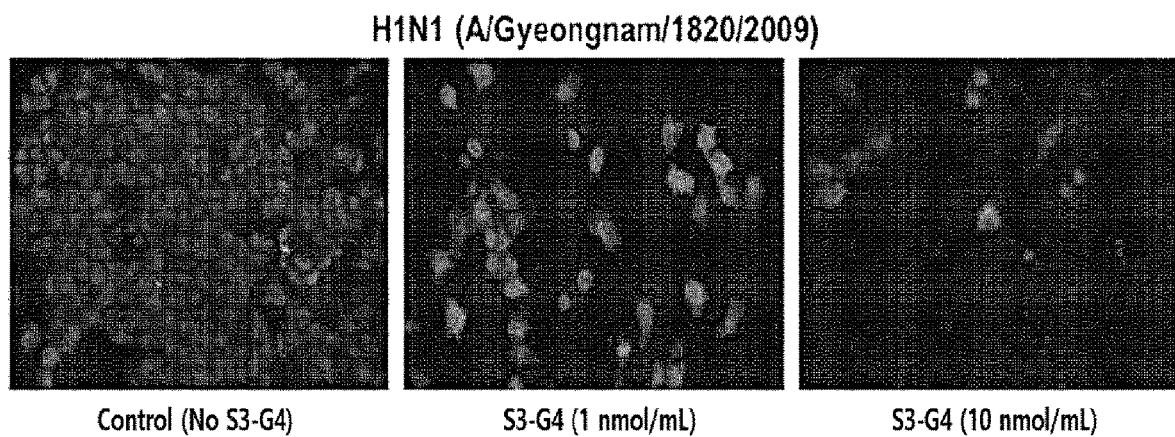
Control (No S3-G4)      S3-G4 (1 nmol/mL)      S3-G4 (10 nmol/mL)

[FIG. 8B]
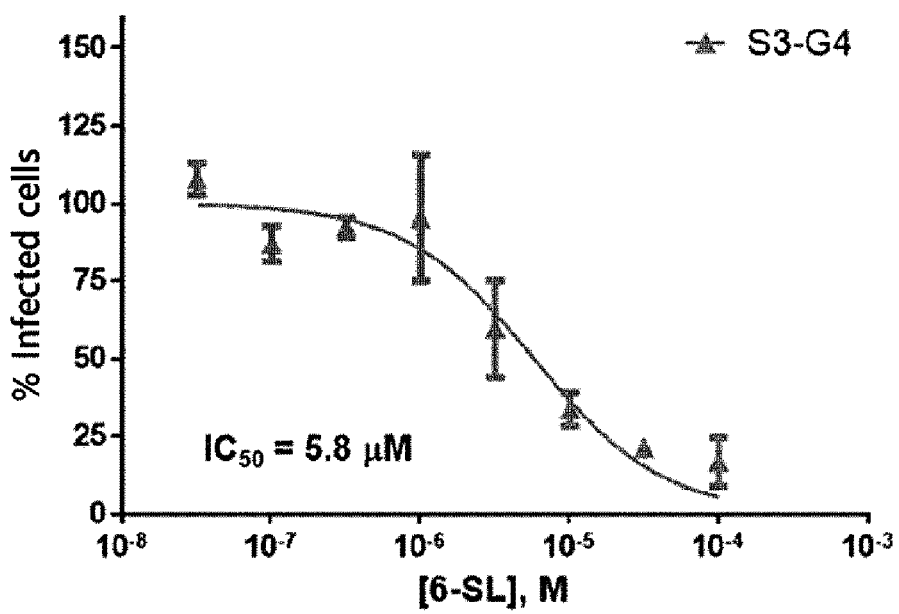

[FIG. 8C]
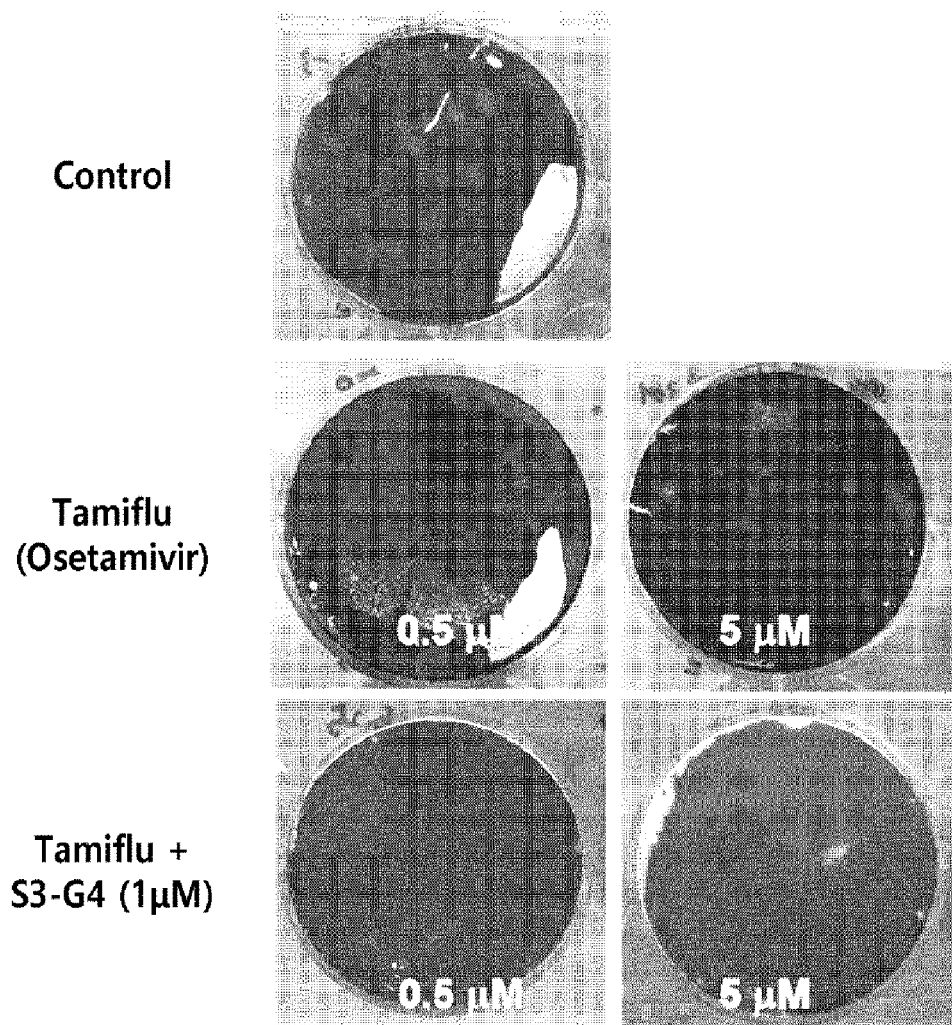

CONJUGATE INCLUDING CORE AND SIALIC ACID OR DERIVATIVE THEREOF BOUND TO SURFACE OF CORE AND USE THEREOF

CROSS-REFERENCE TO RELATED APPLICATIONS

This application claims priority to U.S. Provisional Application No. 62/376,666, filed on Aug. 18, 2016, the content of which is hereby incorporated by reference in its entirety.

BACKGROUND OF THE INVENTION

1. Field of the Invention

The present invention relates to a conjugate including a core and sialic acids or derivatives thereof bound to the surface of the core, and use thereof.

2. Description of the Related Art

Influenza virus is an RNA virus belonging to the family Orthomyxoviridae, which is classified into three serotypes of type A, type B, and type C. Of these, types B and C are found to infect only humans, while type A is found to infect humans, horses, pigs, and other mammals, and also various species of domestic poultry and wild birds. The serotype of influenza virus type A is classified depending on two kinds of proteins found on the surface of the virus, which are hemagglutinin (HA) and neuraminidase (NA). Until now, 144 different serotypes (16 kinds of HA and 9 kinds of NA) were known. HA aids the virus in attaching to somatic cells, while NA helps the virus invade the cells. Influenza virus acquires new antigenicity every winter to cause epidemics, and the virus spreads throughout humans, livestock, and poultry. As it is very important to monitor the virus, there is therefore a demand for the development of primers and probes with high specificity and sensitivity.

Novel influenza A (H1N1) virus, also called "novel flu" or "novel flu virus", has attracted considerable attention and is a new kind of virus in Which genetic materials of influenza viruses originated from human, swine, and birds are mixed, and it was first found in April 2009. Routes of transmission of the virus have not been clarified yet, but it is known that, similar to the seasonal influenza virus, novel influenza A virus is transmitted through droplet infection, that is, mainly from human to human through coughing or sneezing of infected persons at a close distance (within about 2 m). Further, it is known that viruses in foods are killed by cooking the foods at 70° C. or higher.

An incubation period of the novel flu virus is estimated to be 1 to 7 days, and symptoms including upper respiratory symptoms such as fever, chills, headache, cough, sore throat, runny nose, shortness of breath, etc., muscle pain, joint pain, fatigue, vomiting, or diarrhea are observed in patients who are diagnosed with viral infection. It was reported that an infected person is commonly contagious from one day before the onset of symptoms to 7 days following illness onset, and children may be contagious for more than 10 days. In order to reduce damages caused by infection of the novel flu virus, research has been actively conducted to develop a method for early diagnosis of the novel flu viral infection. For example, Korean Patent Publication No. 2011-0064174 discloses a monoclonal antibody specific to novel influenza virus A/H1N1 except for other kinds of influenza virus, a fusion cell producing the antibody, a diagnostic kit including the monoclonal antibody, and a method of diagnosing the novel influenza virus A/H1N1 using the kit. Korean Patent Publication No. 2011-0096940 discloses a diagnostic kit capable of diagnosing type A novel influenza virus (influenza A, H1N1) by rapid immunochromatography using an antibody against hemagglutinin (HA) antigen of the novel influenza virus. Korean Patent Publication No. 2011-0127034 discloses a method of rapidly and accurately detecting the novel flu (A/Korea/01/2009(H1N1)) virus by using influenza type A virus common PCR primers for detecting influenza type A virus and PCR primers specific to detection of swine-derived influenza (novel flu, A/Korea/01/2009(H1N1)) virus.

However, even though the viral infection is diagnosed by these methods, Oseltamivir (product name: Tamiflu) or Zanamivir (product name: Relenza) is merely used as an agent for treating the influenza virus infection. Use of these agents causes generation of resistant viruses, and therefore, development of therapeutic methods for the virus is still unsatisfactory.

Under this background, the present inventors have made extensive efforts to develop a method of effectively treating infection of influenza virus, and as a result, they found that a conjugate including a core and sialic acids or derivatives thereof bound to the surface of the core, wherein the sialic acids or the derivatives thereof are arranged with equal spacing, may be used to treat not only infection of influenza virus but also infection of viruses resistant to the existing anti-viral agents, thereby completing the present invention.

SUMMARY OF THE INVENTION

An object of the present invention is to provide a conjugate including a core and sialic acids or derivatives thereof bound to the surface of the core, wherein the sialic acids or the derivatives thereof are arranged with equal spacing.

Another object of the present invention is to provide a pharmaceutical composition for preventing or treating influenza virus infection, including the conjugate.

Still another object of the present invention is to provide a food composition for preventing or improving influenza virus infection, including the conjugate.

Still another object of the present invention is to provide a method of preventing or treating influenza virus infection, including the step of administering the conjugate into a subject who is suspected of being infected with influenza virus or is infected with influenza virus.

Still another object of the present invention is to provide a method of inhibiting influenza virus infection, including the step of treating isolated influenza virus with the conjugate.

BRIEF DESCRIPTION OF THE DRAWINGS

FIG. 1A is a reaction scheme showing reductive amination of reducing sugar, 6SL, and primary amino groups of PAMAM dendrimers (G2 to G5) using $NaCNBH_3$;

FIG. 1B is a graph showing results of analyzing characteristics of 6SL-PAMAM conjugates by MALDI-TOF MS;

FIG. 1C is a graph showing results of analyzing characteristics of 6SL-PAMAM conjugates by $^1$H-NMR;

FIG. 1D is a schematic diagram showing structures of various 6SL-PAMAM conjugates synthesized in the present invention;

FIG. 1E shows results of analyzing a structure of an S3-G4 conjugate, in which the left figure is a schematic diagram showing a detailed structure of the S3-G4 conjugate and the right figure shows $^1$H-NMR spectra of components constituting the S3-G4 conjugate ($^1$H-NMR spectra of 6SL (top), PAMAM dendrimer (G4, middle), and its conjugate (S3-G4, bottom));

FIG. 2A is a graph showing results of analyzing inhibitory effects of various 6SL-PAMAM conjugates synthesized in the present invention against influenza virus infection;

FIG. 2B is a graph showing results of analyzing the inhibitory effects of 6SL-PAMAM conjugates against influenza virus infection according to ligand spacing;

FIG. 3A shows results of analyzing interaction between a 6SL-PAMAM conjugate and HA, in which the left figure is SPR sensorgrams of the interaction between a 6SL-PAMAM conjugate and HA, and the right figure is a graph showing binding affinity (in response units, RU) of a 6SL-PAMAM conjugate for HA;

FIG. 3B is a schematic diagram showing a structure of an HA trimer, in which the binding site of 6SL is represented by red, and the interval between the binding sites of the 6SL is represented by the black dotted line;

FIG. 3C is a schematic diagram showing interactions between 6SL-PAMAM conjugates (S3-G4 or S6-G4) and binding sites on HA trimers;

FIG. 4 is TEM images showing results of analyzing binding properties between 6SL-PAMAM conjugates (S3-G4) and H1N1 virus, in which the upper left image represents 6SL-PAMAM conjugates (S3-G4), the upper right image represents H1N1 virus, the lower left image represents results of interactions between a PAMAM dendrimer (G4) and H1N1 virus, and the lower right image represents results of interactions between a 6SL-PAMAM conjugate (S3-G4) and H1N1 virus;

FIG. 5 is a fluorescent microscope image showing results of measuring the effects of S3-G4 against single stained virus (R18-labeled H1N1) and dual stained virus (DiOC18 and R18-labeled H1N1) over time;

FIG. 6 is a fluorescent microscope image showing infection-inhibitory activity of S3-G4 against H3N2 virus (A/Shandong/3/93) and different types of H1N1 virus (A/NWS/33, A/Puerto Rico/8/43 and A/California/07/2000));

FIG. 7A is a graph showing the effects of S3-G4 conjugates on viral titers in H1N1 virus-infected mice;

FIG. 7B is a microscopic image showing the effects of S3-G4 conjugates on histopathological signs in lung tissues of H1N1 virus-infected mice;

FIG. 7C is a graph showing the effects of S3-G4 conjugates on cytokine expression levels in lung tissues of H1N1 virus-infected mice;

FIG. 7D is a graph showing the effects of S3-G4 conjugates on survival rates of H1N1 virus-infected mice;

FIG. 7E is a graph showing the effects of S3-G4 conjugates on body weight changes of H1N1 virus-infected mice;

FIG. 8A is a fluorescent microscope image showing the effects of S3-G4 conjugates against infection of antiviral agent-resistant H1N1 virus;

FIG. 8B is a graph showing results of analyzing infection-inhibitory activity of S3-G4 conjugates against antiviral agent-resistant H1N1 virus; and FIG. 8C is an image showing results of analyzing proliferation-inhibitory activity of S3-G4 conjugates against antiviral agent-resistant H1N1 virus.

DETAILED DESCRIPTION OF THE PREFERRED EMBODIMENTS

In an aspect to achieve the above-described objects, the present invention provides a conjugate including a core and sialic acids or derivatives thereof bound to the surface of the core, wherein the sialic acids or the derivatives thereof are arranged with equal spacing.

The term "core", as used herein, refers to a material that functions as a scaffold which binds with sialic acids or derivatives thereof and allows the sialic acids or the derivatives thereof to be arranged with equal spacing.

In the present invention, a material constituting the core is not particularly limited, as long as it includes reactive groups capable of binding with sialic acids or derivatives thereof, and for example, polyamidoamine (PAMAM), polyhydroxybutyrate, polyhydroxyvalerate, polylysine, polylactic acid, polyglycolide, polycaprolactone, polypropylenefumarate, polydioxanone, polynucleotide, or copolymers thereof may be used singly or in combination.

In the present invention, the core preferably has a diameter above a predetermined level, because a plurality of sialic acids or derivatives thereof should be bound to the surface of the core and arranged at equal intervals from one another. The diameter of the core is not particularly limited, as long as a plurality of sialic acids or derivatives thereof are bound to the surface thereof and arranged at equal intervals from one another, and the diameter may be, for example, 3.0 nm to 6.0 nm, for another example, 3.5 nm to 5.5 nm, for still another example, 4.0 nm to 6.0 nm, and for still another example, 4.5 nm to 5.4 nm.

The shape of the core provided in the present invention is not particularly limited, but the shape may be, for example, in a spherical form consisting of polymers of the core-constituting material, for another example, in a layered form through multiple folding of linear polymers of the core-constituting material, and for still another example, in a dendrimer form which is obtained by using the core-constituting material as a base compound.

In an embodiment of the present invention, the core was prepared in a dendrimer form, in which reactive groups included in the core-constituting materials may be regularly arranged, and thus sialic acids or derivatives thereof bound thereto may be arranged with equal spacing.

The term "dendrimer", as used herein, refers to a macromolecule which is a spherical structure formed by repeated tree-like (dendron) molecular branching of a base compound. The dendrimer is used to easily form nano-sized particles having an accurate molecular weight and structure. Since the dendrimer possesses many reactive groups on the outer surface, it exhibits chemically or physically unique characteristics, and many different derivatives and reactive groups may be introduced at the terminal groups abundant on the surface. In particular, it is easy to control dendrimers and to predict their structures, compared to linear polymer forms, and therefore, dendrimers may be applied to a variety of fields.

The generations of dendrimers may be specified according to the level of layering of the base compound forming the dendrimers. For example, when one base compound is polymerized without being bonded to itself, it may be expressed as a first-generation dendrimer (G1). When one base compound is additionally bound to the terminal of the base compound included in the first-generation dendrimer, it may be expressed as a second-generation dendrimer (G2). When one base compound is additionally bound to the terminal of the base compound included in the second-generation dendrimer, it may be expressed as a third-generation dendrimer (G3). When one base compound is is additionally bound to the terminal of the base compound included in the third-generation dendrimer, it may be expressed as a fourth-generation dendrimer (G4). When one base compound is additionally bound to the terminal of the base compound included in the fourth-generation dendrimer, it may be expressed as a fifth-generation dendrimer (G5). That is, as one base compound is further bound, the number of generations is increased by one generation.

In the present invention, the dendrimer utilizes a material constituting the above-described core as a base compound. The base compound is not particularly limited, as long as a plurality of sialic acids or derivatives thereof are bound to the surface thereof and arranged at equal intervals from one another. The base compound may be, for example, polyamidoamine, polylysine, polynucleotide, etc., and for another example, polyamidoamine.

The term "sialic acid", as used herein, also called neuraminic acid, refers to an amino sugar having a N-acetylated, N-glycosylated, or O-acetylated chemical structure of neuraminic acid, which is an aldol condensation product of pyruvic acid with mannosamine.

In the present invention, the sialic acid may be used as a ligand that binds with hemagglutinin (HA) of virus to inhibit its function, and not only sialic acid but also a derivative thereof may be used as the ligand.

The term "derivative", as used herein, refers to a similar compound obtained by chemically modifying a portion of a desired compound, and it may generally be a compound obtained by replacing a hydrogen atom or a specific atomic group in the desired compound by another atom or atomic group.

In the present invention, the derivative may be interpreted as a derivative of sialic acid, and the derivative of sialic acid is not particularly limited, as long as it binds with HA of virus to inhibit its function. The derivative may be, for example, a sialyl oligosaccharide in which sialic acid binds to a saccharide, and for another example, 3'-sialyllactose, 6'-sialyllactose, sialyl lacto-N-tetraose, disialyl lacto-N-tetraose, etc.

A distance between the sialic acids or derivatives thereof included in the conjugate provided in the present invention is not particularly limited, but the distance is may be 1.0 nm or more, 1.2 nm or more, 1.6 nm or more, 1.9 nm or more, 2.0 nm or more, 2.1 nm or more, 2.4 nm or more, 3.1 nm or more, 1.0 nm to 4.0 nm, 1.2 nm to 4.0 nm, 1.6 nm to 4.0 nm, 1.9 nm to 4.0 nm, 2.0 nm to 4.0 nm, 2.1 nm to 4.0 nm, 2.4 nm to 4.0 nm, or 3.1 nm to 4.0 nm.

For example, in the case of a conjugate including a polyamidoamine dendrimer as a core and 6'-sialyllactose (6SL) as a sialic acid derivative binding to the core, the distance between 6SLs may be, but is not particularly limited to, for example, 1.0 nm to 4.0 nm, for another example, 1.6 nm to 3.5 nm, for still another example, 2.0 nm to 3.1 nm, and for still another example, 2.4 nm or 3.1 nm.

The term "conjugate", as used herein, refers to a material in which a plurality of sialic acids or derivatives thereof is bound to one core. Specifically, the conjugate may be in a form in which the sialic acids or the derivatives thereof are bound to the core with equal spacing. Further, the conjugate of the present invention may be in a form in which the sialic acids or the derivatives thereof are bound to the core via a reactive group of the core or a plurality of the sialic acids or the derivatives thereof are bound to the core via a linker. In this regard, the reactive group of the core is not particularly limited, as long as it allows the sialic acids or the derivatives thereof to be bound to the core. A reactive group known in the art may be used.

As described above, the component or shape of the core is not limited, as long as the sialic acids or the derivatives thereof are bound to the core, and therefore, the conjugate may be in various forms by combination of the core and the sialic acids or the derivatives thereof.

For example, a conjugate including a polyamidoamine (PAMAM) dendrimer as the core and 6'-sialyllactose (6SL) as the sialic acid derivative bound to the core may be a conjugate (6SL-PAMAM), in which 10 to 128 6SLs are bound to the terminal amine groups of a second to fifth generation PAMAM dendrimer.

In the 6SL-PAMAM conjugate, the number of 6SL bound to the PAMAM dendrimer may vary depending on the generation of the PAMAM dendrimer used. For example, in a 6SL-PAMAM conjugate including a third generation PAMAM dendrimer, 10 to 32 6SLs may be bound to the terminal amine group of the dendrimer. For another example, in a 6SL-PAMAM conjugate including a fourth generation PAMAM dendrimer, 20 to 64 6SLs may be bound to the terminal amine group of the dendrimer. For still another example, in a 6SL-PAMAM conjugate including a fifth generation PAMAM dendrimer, 20 to 128 6SLs may be bound to the terminal amine group of the dendrimer.

More specifically, the generations of the used dendrimers are as follows:

First, in the case of a 6SL-PAMAM conjugate including a fourth generation PAMAM dendrimer, for example, 20 to 64 6SLs may be bound to the terminal amine group of the dendrimer, for another example, 20 to 40 6SLs may be bound thereto, for still another example, 20 to 31 6SLs may be bound thereto, for still another example, 20 to 26 6SLs may be bound thereto, and for still another example, 20 6SLs may be bound thereto.

Next, in the case of a 6SL-PAMAM conjugate including a fifth generation PAMAM dendrimer, for example, 20 to 128 6SLs may be bound to the terminal amine group of the dendrimer, for another example, 30 to 80 6SLs may be bound thereto, for still another example, 30 to 77 6SLs may be bound thereto, for still another example, 30 to 56 6SLs may be bound thereto, for still another example, 30 to 48 6SLs may be bound thereto, for still another example, 30 to 40 6SLs may be bound thereto, and for still another example, 37 6SLs may be bound thereto.

According to an embodiment of the present invention, many different types of 6SL-PAMAM conjugates were prepared by reductive amination of the aldehyde group of the reducing sugar in 6SL with the amino groups of PAMAM dendrimers having an ethylenediamine core (G2 to G5) (FIGS. 1A and 1D). The number of 6SL included therein was determined (Table 4).

Subsequently, the ability of the 6SL-PAMAM conjugates to inhibit influenza virus infection was analyzed in vitro, and as a result, it was confirmed that a predetermined size of dendrimer is required (FIG. 2A) and inter-6SL ligand spacing is related to inhibition efficiency of H1N1 virus infection (Table 5, FIG. 2B). It was also confirmed that when a neuraminidase (NA) inhibitor and the 6SL-PAMAM conjugate were treated in combination, the inhibitory effect against H1N1 virus infection was increased (Table 8).

Next, binding affinity of the 6SL-PAMAM conjugate for HA was analyzed. As a result, it was confirmed that all of the 6SL-PAMAM conjugates (S3-G4, S4-G4, and S7-G5) with 2.4 nm or more of inter-6SL ligand spacing show high binding affinity for HA protein (FIG. 3A).

In another aspect, the present invention provides a pharmaceutical composition for preventing or treating influenza virus infection, including the conjugate.

The term "influenza virus", as used herein, refers to a pathogen that is a major cause of viral respiratory diseases, and is largely divided into A, B, and C types according to antigenic differences of NP (nucleocapsid) and M (matrix) proteins. Of these, type A is sub-divided into H1 type to H16 type according to antigenicity of hemagglutinin protein, and sub-divided into N1 type to N9 type according to antigenicity of neuramidase protein.

In the present invention, the influenza virus is not particularly limited. However, the influenza virus may be, for example, influenza A virus or influenza B virus, and for another example, novel influenza A (H1N1) virus.

The term "novel influenza A (H1N1) virus", as used herein, is also designated as "novel flu virus", "H1N1", or "H1N1 virus", and generated by mutation of type A influenza virus. Its serotype, which is determined on the basis of two proteins on the surface of the virus, hemagglutinin (HA) and neuraminidase (NA), is H1N1. The novel influenza A (H1N1) virus refers to a virus that infects persons to cause new respiratory diseases.

The term "influenza virus infection", as used herein, refers to a pathological disease caused by infection of a subject with influenza virus. For example, "novel flu", which is a disease caused by infection with a mutant strain of type A influenza virus, is known to show symptoms including upper respiratory symptoms such as fever, chills, headache, cough, sore throat, runny nose, shortness of breath, etc., muscle pain, joint pain, fatigue, vomiting, diarrhea, etc.

The term "prevention", as used herein, means all of the actions by which the symptoms of influenza virus infection are restrained or retarded by administering the conjugate or the pharmaceutical composition including the same provided in the present invention.

The term "treatment", as used herein, means all of the actions by which the symptoms of influenza virus infection are improved or modified favorably by administering the conjugate or the pharmaceutical composition including the same provided in the present invention.

A content of the conjugate which is included in the pharmaceutical composition provided in the present invention is not particularly limited, as long as it is able to exhibit prophylactic or therapeutic effects on influenza virus infection, and the content may be, for example, 0.0001% by weight to 50% by weight, and for another example, 0.01% by weight to 10% by weight, with respect to the total composition.

The pharmaceutical composition of the present invention may further include a pharmaceutically acceptable carrier, excipient, or diluent commonly used in the preparation of the pharmaceutical composition. The carrier may include a non-naturally occurring carrier.

The term "pharmaceutically acceptable", as used herein, means no toxicity to cells or humans exposed to the composition.

Specifically, the pharmaceutical composition may be formulated into oral preparations such as powders, granules, tablets, capsules, suspensions, emulsions, syrups, aerosols, or the like, and preparations for external application, suppository, or sterile injectable solution according to common methods. In the present invention, the carrier, excipient, and diluent which may be included in the pharmaceutical composition may include lactose, dextrose, sucrose, sorbitol, mannitol, xylitol, erythritol, maltitol, starch, acacia rubber, alginate, gelatin, calcium phosphate, calcium silicate, cellulose, methyl cellulose, microcrystalline cellulose, polyvinyl pyrrolidone, water, methylhydroxybenzoate, propylhydroxybenzoate, talc, magnesium stearate, and mineral oil. The formulation may involve using general diluents or excipients such as fillers, bulking agents, binders, wetting agents, disintegrants, surfactants, etc. Solid formulations for oral administration may include tablets, pills, powders, granules, capsules, etc. The solid formulations may be prepared by mixing with at least one excipient, for example, starch, calcium carbonate, sucrose, lactose, gelatin, etc. In addition to such general excipients, lubricants such as magnesium stearate or talc may also be used. Liquid formulations for oral administration may include suspensions, solutions for internal use, emulsions, syrups, etc. In addition to simple diluents commonly used, such as water and liquid paraffin, many different excipients may also be used, for example, wetting agents, flavors, fragrances, preserves, etc. Formulations for parenteral administration may include sterile aqueous solutions, non-aqueous solvents, suspensions, emulsions, lyophilized preparations, or suppositories. The non-aqueous solutions and the suspensions may include propylene glycol, polyethylene glycol, vegetable oil such as olive oil, injectable ester such as ethyloleate, etc. The base for suppositories may include witepsol, macrogol, tween 61, cacao butter, laurin butter, glycerogelatin, etc.

Figure 4:
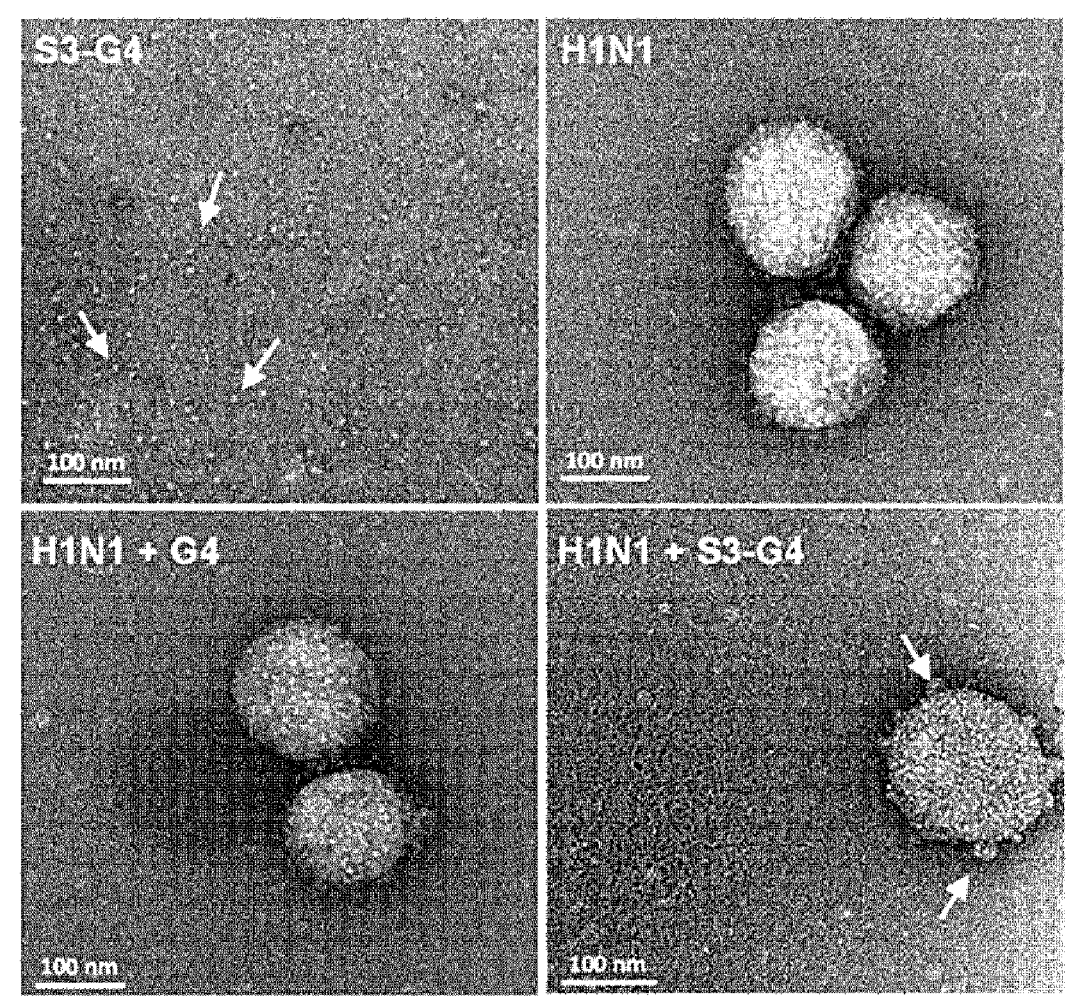

According to an embodiment of the present invention, effects of the 6SL-PAMAM conjugates of the present invention against virus infection were analyzed by electron microscopy. As a result, it was analyzed that the 6SL-PAMAM conjugates bind with hemagglutinin (HA) on the surface of virus to form bleb on the surface of virus, leading to inhibition of viral attachment, cell entry, and endosomal fusion/escape (FIG. 4). Further, immunofluorescence assay showed that the 6SL-PAMAM conjugates are involved in cell entry of virus (FIG. 5). Furthermore, it was confirmed that the 6SL-PAMAM conjugates exhibit effects of reducing the expression level of NA which is increased by virus infection (FIG. 6).

Therefore, the results of analyzing effects of 6SL-PAMAM conjugates against virus infection in vivo showed that the 6SL-PAMAM conjugates reduce viral titers in the lung tissues of infected hosts (FIG. 7A), histopathological signs of virus infection (FIG. 7B), and cytokine (IL-6 and CCL2) levels by virus infection (FIG. 7C), increase survival rates of infected hosts (FIG. 7D), and recover loss of body weight by virus infection (FIG. 7E).

Lastly, effects of 6SL-PAMAM conjugates against infections of antiviral agent-resistant viruses were analyzed. As a result, it was confirmed that the 6SL-PAMAM conjugates exhibit inhibitory activity against infections of influenza viruses resistant to existing antiviral agents (FIGS. 8A to 8C).

In still another aspect, the present invention provides a method of preventing or treating influenza virus infection, including the step of administering the conjugate or the pharmaceutical composition including the conjugate into a subject who is suspected of being infected with influenza virus or is infected with influenza virus.

The term "subject", as used herein, refers to a living organism which has had already influenza virus infection or has possibility of having influenza virus infection. The subject may be, for example, high vertebrates having respiratory organs, for another example, mammals, for still another example, primates, and for still another example, humans, rats, mice, livestock, etc.

The term "administration", as used herein, means introduction of a predetermined substance into a patient by a certain suitable method. An active ingredient may be formulated for human or veterinary use, and then administered via various routes. An administration route of the pharmaceutical composition including the conjugate of the present invention is not particularly limited, but the composition may be administered, for example, via parenteral routes, such as an intravascular, intravenous, intra-arterial, intramuscular, or subcutaneous route, for another example, via oral, nasal, rectal, or transdermal route, or via the inhalation route using aerosol, and for still another example, via bolus injection or slow infusion.

The conjugate or the pharmaceutical composition including the conjugate of the present invention may be administered in a pharmaceutically effective amount.

As used herein, the phrase "pharmaceutically effective amount" refers to an amount sufficient to treat diseases, at a reasonable benefit/risk ratio applicable to any medical treatment, and further an amount that will not cause an adverse reaction. An effective dose level may be readily determined by those skilled in the art, depending on a variety of factors including patient's sex, age, body weight, health condition, the kind of disease, severity, activity of the drug, sensitivity to the drug, administration method, administration time, administration route, excretion rate, duration of treatment, drugs used in combination or concurrently, and other factors known in the medical field.

The conjugate of the present invention may be administered, for example, in an amount of $1\times10^7$ to $1\times10^{11}$ conjugates, for another example, $1\times10^8$ to $5\times10^{10}$ conjugates, and for still another example, $5\times10^8$ to $2\times10^{10}$ conjugates, but is not limited thereto.

For another example, the pharmaceutical composition of the present invention may be administered at a daily dose of 0.0001 mg/body weight (kg) to 100 mg/body weight (kg), and more specifically, 0.001 mg/body weight (kg) to 100 mg/body weight (kg), based on solids. Administration may be performed with the above-recommended administration dose once a day or several times a day.

In the method of preventing or treating influenza virus infection of the present invention, administration route and mode are not particularly limited, and the pharmaceutical composition including the conjugate may be administered according to any administration route and mode, as long as it is able to reach a desired site. Specifically, the pharmaceutical composition may be administered via a variety of routes including oral or parenteral routes, and non-limiting examples of the administration route may include an oral, rectal, topical, intravenous, intraperitoneal, intramuscular, intra-arterial, transdermal, or intranasal route, or inhalation.

In still another aspect, the present invention provides a food composition for preventing or improving influenza virus infection, including the conjugate.

The term "improvement", as used herein, means all of the actions by which parameters, for example, the degree of symptoms associated with the condition being treated by administration of the composition including the conjugate of the present invention are at least reduced.

The term "food", as used herein, includes meats, sausages, bread, chocolate, candies, snacks, cookies, pizza, ramen, other noodles, chewing gums, dairy products including ice cream, soups, beverages, teas, drinks, alcoholic drinks, vitamin complexes, health functional foods, health foods, or the like, and generally includes all foods.

Since the food composition of the present invention may be ingested routinely, the effect of improving influenza virus infection at a high level may be expected, and therefore, the food composition may be very usefully applied for the purpose of promoting health.

The term "functional food" is identical to the term food for special health use (FoSHU), and is a food having medicinal effects, which is processed so as to efficiently exhibit biologically modulating function as well as to supply nutrition. The term 'functional', as used herein, means that it is taken for the purpose of controlling nutrients with respect to structures and functions of the human body or of obtaining effects beneficial for health care, such as physiological effects. The food composition of the present invention may be prepared by a method commonly used in the art. The food composition may be prepared by adding raw materials and components commonly added in the art upon preparation. Further, formulations of the food may also be prepared without limitation as long as they are formulations acceptable as foods. The food composition of the present invention may be prepared in various types of formulations. Unlike general drugs, the food composition includes a food as a raw material, and therefore, it has advantages of being free from side effects that may occur when taken for a long period of time. The food composition is also excellent in portability, and therefore, the food of the present invention may be taken as a supplement agent for promoting the effect of improving influenza virus infection.

The health food refers to a food having an effect of actively maintaining or promoting health, compared to a general food, and a health supplement food refers to a food aimed at health supplement. In some cases, the terms "health functional foods", "health foods", and "health supplement foods" are used interchangeably.

Specifically, the health functional food is a food prepared by adding the compound of the present invention to a food material such as beverages, teas, flavors, gums, confectionery, etc., or prepared as a capsule, powder, or suspension, and the health functional food means a food that brings out a particular effect on health when taken. Unlike general drugs, the food composition includes a food as a raw material, and therefore, it has advantages of being free from side effects that may occur when taken for a long period of time.

The food composition may further include a physiologically acceptable carrier, and the kind of the carrier is not particularly limited, and any carrier may be used as long as it is commonly used in the art.

Further, the food composition may further include an additional ingredient capable of improving smell, taste, appearance, etc. which is commonly used in the food composition. For example, the food composition may include vitamin A, C, D, E, B1, B2, B6, or B12, niacin, biotin, folate, panthotenic acid, etc. Further, the food composition may include minerals such as zinc (Zn), iron (Fe), calcium (Ca), chromium (Cr), magnesium (Mg), manganese (Mn), copper (Cu) chromium (Cr), etc.; and amino acids such as lysine, tryptophan, cysteine, valine, etc.

Further, the food composition may include food additives such as preservatives (potassium sorbate, sodium benzoate, salicylic acid, sodium dehydroacetate, etc.), disinfectants (bleaching powder, higher bleaching powder, sodium hypochlorite, etc.), antioxidants (butylhydroxyanisole (BHA), butylhydroxytoluene (BHT), etc.), coloring agents (tar color, etc.), color-developing agents (sodium nitrite, etc.), bleaching agents (sodium sulfite), seasonings (monosodium glutamate (MSG), etc.), sweeteners (dulcin, cyclemate, saccharin, sodium, etc.), flavors (vanillin, lactones, etc.), swelling agents (alum, potassium D-bitartrate, etc.), fortifiers, emulsifiers, thickeners (adhesive pastes), film-forming agents, gum base agents, antifoaming agents, solvents, improvers, etc. The additives may be selected and used in an appropriate amount according to the food types.

The food composition of the present invention may be used as, for example, a health drink composition, and in this case, it may include additional ingredients such as various flavors, natural carbohydrates, etc., like common drinks. The above-described natural carbohydrates may include monosaccharides such as glucose and fructose; disaccharides such as maltose and sucrose; polysaccharides such as dextrin and cyclodextrin; sugar alcohols such as xylitol, sorbitol, erythritol, etc. The sweetener may include a natural sweetener such as thaumatin and stevia extract; or an artificial sweetener such as saccharin and aspartame. A ratio of the natural carbohydrate per 100 mL of the health drink composition of the present invention may generally be about 0.01 g to about 0.04 g, and specifically, about 0.02 g to about 0.03 g.

In addition to the above ingredients, the health drink composition may include a variety of nutrients, vitamins, electrolytes, flavoring agents, coloring agents, pectic acid and salts thereof, arginic acid and salts thereof, organic acid, protective colloidal viscosifiers, pH regulators, stabilizers, preservatives, glycerin, alcohols, carbonators, etc. The health drink composition may also include natural fruit juice, fruit juice beverages, or fruit flesh for the preparation of vegetable beverages. All of these ingredients may be added singly or in any combination thereof. A mixing ratio of those ingredients does not matter, but is generally selected in the range of 0.01 to 0.1 parts by weight per 100 parts by weights of the health drink composition of the present invention.

In still another aspect, the present invention provides a method of inhibiting influenza virus infection, including the step of treating influenza virus with the conjugate.

As described above, the sialic acids or derivatives thereof included in the conjugates of the present invention bind with hemagglutinin on the surface of influenza virus to form bleb, leading to inhibition of viral attachment, cell entry, and endosomal fusion/escape, and the conjugates are involved in cell entry of virus and exhibit effects of reducing the expression level of NA which is increased by virus infection.

Therefore, the conjugate of the present invention may be used for inhibiting influenza virus infection in vitro, in vivo, or ex vivo.

In particular, when it is intended to inhibit influenza virus infection in vitro or ex vivo in order to study infectiousness of influenza virus for target cells, the conjugates may be diluted with a buffer at a proper concentration, and then treated to a virus solution or virus-infected cells, thereby inhibiting influenza virus infection of the cells.

Effect of the Invention

The conjugate provided in the present invention binds with hemagglutinin on the surface of influenza virus to inhibit the course of infection of influenza virus, thereby preventing or treating infection of influenza virus and also preventing or treating infection of influenza virus resistant to antiviral agents. Accordingly, the conjugate may be widely used in the development of prophylactic or therapeutic agents for influenza virus infection.

Hereinbelow, the present invention will be described in detail with accompanying exemplary embodiments. However, the exemplary embodiments disclosed herein are only for illustrative purposes and should not be construed as limiting the scope of the present invention.

Example 1

Synthesis of 6SL-PAMAM Conjugate

6SL-PAMAM conjugates were prepared by a reductive amination of the aldehyde group of the reducing sugar in 6SL with the amino groups of PAMMAM dendrimers having an ethylenediamine core (G2 to G5) (FIG. 1a).

Briefly, each PAMAM dendrimer (20 mg) was mixed with a different amount of 6SL solution in sodium borate buffer (0.1 M; pH 9.5) containing NaCNBH$_3$ (50 mM) (Table 1).

TABLE 1

| Mixture ratio of PAMAM dendrimer and 6SL ligand | |
|---|---|
| Conjugate | Reaction molar ratio (PAMAM:6SL) |
| S1-G2 | 1:64 |
| S2-G3 | 1:128 |
| S3-G4 | 1:32 |
| S4-G4 | 1:64 |
| S5-G4 | 1:128 |
| S6-G4 | 1:256 |
| S7-G5 | 1:64 |
| S8-G5 | 1:128 |
| S9-G5 | 1:256 |
| S10-G5 | 1:512 |

The reaction solution was reacted continuously for 5 days at room temperature in darkness with gentle stirring. Upon completion of the reaction, the unreacted reagents were removed by filtering using Amicon centrifugal filters (Millipore) with appropriate molecular cutoff (MWCO 3 K or 10 K), and then change the solvent to deionized water. After filtration, the solutions were freeze-dried and the obtained white powdery samples were stored under desiccation until use.

Example 2

Feature Analysis of 6SL-PAMAM Conjugate

Features of the 6SL-PAMAM conjugates synthesized in Example 1 were analyzed using MALDI-TOF MS (Bruker Daltonics) and $^1$H-NMR.

Example 2-1

MALDI-TOF MS Analysis

MALDI-TOF MS analysis was carried out using a nitrogen laser (337 nm). In particular, 50% acetonitrile containing 2,5-dihydroxybenzoic acid (10 mg/mL) was used as a matrix. The analyte-matrix solution was prepared at a ratio of 1:2 (analyte: matrix, v/v). The prepared analyte-matrix solution (1 μl) was deposited onto the sample plate and dried by vacuum evaporation. Additionally, at least 100 shots per spectrum were imaged using a linear positive ion mode. The analysis of the imaged data was carried out using Bruker Daltonics Microflex Analysis Software (FIG. 1b), and the average numbers of 6SL attached to PAMAM were calculated from the data analysis above (Table 2).

TABLE 2

| Average number of 6SL attached to PAMAM measured via MALDI-TOF MS analysis | |
|---|---|
| Conjugate | Number of 65L |
| S1-G2 | N.D. |
| S2-G3 | 25.1 |
| S3-G4 | 20.7 |
| S4-G4 | 27.1 |

TABLE 2-continued

Average number of 6SL attached to PAMAM
measured via MALDI-TOF MS analysis

| Conjugate | Number of 65L |
|---|---|
| S5-G4 | 32.1 |
| S6-G4 | 41.4 |
| S7-G5 | 37.2 |
| S8-G5 | 48.6 |
| S9-G5 | 52.2 |
| S10-G5 | 72.2 |

Example 2-2

$^1$H-NMR Analysis

NMR spectra for G2-G5 dendrimers, 6SL, and conjugates thereof were measured using a Bruker Ascend™ 500 spectrometer in deuterium oxide (FIG. 1c), and the average numbers of 6SL attached to PAMAM were calculated from the data analysis above (Table 3 and FIG. 1c).

As shown in FIG. 1c, the $^1$H NMR spectra of the PAMAM dendrimers showed signals at 2.45 ppm to 2.50 ppm assignable to the —$CH_2$-adjacent to the amide bond within the PAMAM dendrimer. The integral of these signals was used as an internal standard, being set at 56H for G2, 120 H for G3, 245 H for G4, and 504H for G5. The integral of the distinctive signal at 2.07 ppm, corresponding to the —$CH_3$ of the 6SL acetyl group, was used to determine the number of 6SL ligands on each dendrimer.

TABLE 3

Average number of 6SL attached to
PAMAM measured via $^1$H-NMR analysis

| Conjugate | Number of 6SL |
|---|---|
| S1-G2 | 12.8 |
| S2-G3 | 25.5 |
| S3-G4 | 20.4 |
| S4-G4 | 26.4 |
| S5-G4 | 30.8 |
| S6-G4 | 40.3 |
| S7-G5 | 37.4 |
| S8-G5 | 48.1 |
| S9-G5 | 55.7 |
| S10-G5 | 76.9 |

Based on the results above, it was possible to predict the general structure of the synthesized 6SL-PAMAM conjugates (Table 4 and FIG. 1d).

TABLE 4

Number of 6SL attached to PAMAM

| Conjugate | Number of 6SL |
|---|---|
| S1-G2 | 13 |
| S2-G3 | 26 |
| S3-G4 | 20 |
| S4-G4 | 26 |
| S5-G4 | 31 |
| S6-G4 | 40 |
| S7-G5 | 37 |
| S8-G5 | 48 |
| S9-G5 | 56 |
| S10-G5 | 77 |

The results of the $^1$H-NMR analysis of the S3-G4 conjugates obtained from the results above and the structure of the conjugate derived therefrom are shown in FIG. 1e.

Example 3

Analysis of Influenza Infection Inhibition of 6SL-PAMAM Conjugate Under in Vitro Assay Condition Analysis of infection inhibition under an in vitro assay condition was carried out using a method of evaluating the ability of the 6SL-PAMAM conjugates inhibiting influenza infection.

First, half-log serial dilutions of the test conjugates were prepared using PBS. The prepared dilutions (50 μL) were mixed with an equal volume of H1N1 strains (A/California/04/2009 or oseltamivir-resistant H1N1, A/Gyeongnam/1820/2009) at $1\times10^3$ $TCID_{50}$. The mixture above was incubated at 37° C. for 1 hour, and then 100 μL of MDCK cells ($1.5\times10^5$ cells/mL) were added. Thereafter, the mixture was further incubated at 37° C. for another 18 hours under a condition of 5% $CO_2$. Upon completion of the incubation, fixing solutions (acetone:PBS=4:1, v/v) were added to the incubated MDCK cells, and fixed for 10 to 15 minutes. In addition, an ELISA analysis using an anti-NA murine antibody (Millipore) and an anti-mouse goat antibody-HRP conjugate (Jackson Immunoresearch) was carried out in order to detect influenza nucleoprotein (NP) which was contained in each MDCK cell (FIG. 2a). Absorbance relative to the negative control (uninfected cells; 0% infection) and the positive control (infected cells without inhibitor; 100% infection) was used to calculate the infection rate for each MDCK cell. Statistical analysis of the calculated infection rate was determined using GraphPad Prism 6.0 (GraphPad Software, San Diego, Calif.).

As shown in FIG. 2a, in the case of S1-G2 and S2-G3, which are relatively small in size (G2 and G3 dendrimers have diameter smaller than 4 nm), no inhibition of viral infection was observed. Additionally, with the exception of S6-G4, it was confirmed that all of the 6SL conjugates including G4 and G5 dendrimers (diameter greater than 4.5 nm) inhibited H1N1 infection.

These results suggest that a constant dendrimer scaffold size is required for the inhibition of H1N1 under an in vitro assay condition.

Additionally, FIG. 2a shows the result that the efficacy of H1N1 infection inhibition decreased as the number of 6SL attached to the PAMAM conjugate increased. This result is inconsistent with the well-established principle that the binding affinity of multivalent ligands increases with ligand valency (e.g., number of ligands).

Considering that valency and inter-ligand spacing are used as factors to develop potent inhibitors against anthrax toxin, it was attempted to confirm whether the distance between 6SL ligands contained in 6SL-PAMAM conjugates was correlated with the efficacy of H1N1 infection inhibition.

Accordingly, the surface area ($4\pi r^2$) of the dendrimer was calculated using the diameter of a PAMAM dendrimer contained in 6SL-PAMAM conjugates, and then the surface area was divided by the number of 6SL ligands to calculate the distance between the 6SL ligands. Thereafter, the correlation between the calculated distance between the 6SL ligands and the efficacy of H1N1 infection inhibition was analyzed (Table 5 and FIG. 2b).

TABLE 5

Effect of 6SL-PAMAM conjugate inhibiting H1N1 infection under in vitro assay condition

| Conjugate | Diameter (nm) of PAMAM dendrimer | Number of 6SL attached to PAMAM | Average distance (nm) between 6SL ligand | IC$_{50}$ (μM) | logIC$_{50}$ (M) |
|---|---|---|---|---|---|
| S1-G2 | 2.9 | 13 | 2.1 | — | — |
| S2-G3 | 3.6 | 26 | 1.6 | — | — |
| S3-G4 | 4.5 | 20 | 3.1 | 3.4 | −5.5 ± 0.3 |
| S4-G4 | 4.5 | 26 | 2.4 | 12 | −4.9 ± 0.3 |
| S5-G4 | 4.5 | 31 | 2.0 | 58 | −4.2 ± 0.3 |
| S6-G4 | 4.5 | 40 | 1.6 | — | — |
| S7-G5 | 5.4 | 37 | 2.4 | 8.1 | −5.1 ± 0.4 |
| S8-G5 | 5.4 | 48 | 1.9 | 10.7 | −5.0 ± 0.3 |
| S9-G5 | 5.4 | 56 | 1.6 | 21.8 | −4.7 ± 0.3 |
| S10-G5 | 5.4 | 77 | 1.2 | 220 | −3.7 ± 0.7 |

As shown in Table 5 and FIG. 2b, it was confirmed that the distance between 6SL ligands and the efficacy of H1N1 infection inhibition were correlated.

Specifically, in the case of the 6SL-PAMAM conjugates (S1-G2 and S2-G3) containing G2 and G3, the distance between 6SL ligands was narrow and the H1N1 infection inhibitory effect was not observed. Whereas, in the case of the 6SL-PAMAM conjugates (S3-G4, S4-G4, S5-G4, and S6-G4) containing G4, the H1N1 infection inhibitory effect was reduced as the distance between 6SL ligands decreased. Additionally, in the case of the 6SL-PAMAM conjugates (S7-G5, S8-G5, S9-G5, and S10-G5) containing G5, the H1N1 infection inhibitory effect was also reduced as the distance between 6SL ligands decreased.

However, it was observed that the H1N1 infection inhibitory effects varied depending on the ethylenediamine core (G4 or G5) contained in the 6SL-PAMAM conjugates even when the distance between 6SL ligands was the same.

On the other hand, since neuraminidase (NA) of H1N1 virus is able to hydrolyze 6SL ligands, it can limit the H1N1 infection inhibitory effect of the 6SL-PAMAM conjugates.

Accordingly, it was attempted to confirm whether the treatment with oseltamivir carboxylate (OC), an inhibitor of the NA, may affect the H1N1 infection inhibitory effect of the 6SL-PAMAM conjugates.

In order to analyze the H1N1 infection inhibitory effect of the 6SL-PAMAM conjugates, the same experiment as described above was carried out except that it comprised a step of mixing the 6SL-PAMAM conjugates and H1N1 strains under conditions of treatment with OC (1 μM) and without (Table 6).

TABLE 6

Effect of 6SL-PAMAM conjugate inhibiting H1N1 infection depending on treatment with OC

| | IC$_{50}$ (μM) | | logIC$_{50}$ (M) | |
|---|---|---|---|---|
| Conjugate | Untreated with OC | OC (1 μM) | Untreated with OC | OC (1 μM) |
| S1-G2 | — | — | — | — |
| S2-G3 | — | — | — | — |
| S3-G4 | 3.4 | 1.7 | −5.5 ± 0.3 | −5.8 ± 0.6 |
| S4-G4 | 12 | 3.4 | −4.9 ± 0.3 | −5.5 ± 0.5 |
| S5-G4 | 58 | 13.6 | −4.2 ± 0.3 | −4.9 ± 0.5 |
| S6-G4 | — | — | — | — |
| S7-G5 | 8.1 | 2.5 | −5.1 ± 0.4 | −5.6 ± 0.7 |
| S8-G5 | 10.7 | 3.2 | −5.0 ± 0.3 | −5.5 ± 0.7 |
| S9-G5 | 21.8 | 4.4 | −4.7 ± 0.3 | −5.4 ± 0.5 |
| S10-G5 | 220 | 19.7 | −3.7 ± 0.7 | −4.7 ± 0.5 |

Example 4

Analysis of Binding Affinity of 6SL-PAMAM Conjugate on HA

HA proteins, which are the surface antigens of H1N1 virus, were immobilized on CM5 chips according to the standard amine coupling protocol (GE healthcare, Uppsala, Sweden). Thereafter, the binding affinity of the HA and 6SL-PAMAM conjugate was analyzed through surface plasmon resonance (SPR) analysis, which was used to obtain the molecular reaction/rate data between 6-SL PAMAM conjugates and HA proteins.

Briefly, the carboxymethyl group on the surface of the CM5 chips was activated by adding 35 mL (flow rate, 5 mL/min) of an equimolar mixture of N-ethyl-N-(dimethylaminopropyl) carbodiimide and N-hydroxysuccinimide (final concentration 0.05 M). Thereafter, HA was diluted to 50 μg/mL in 100 mM sodium acetate buffer (pH 5.0), and added to the surface of the activated CM5 chips, and then treated with 1 M ethanolamine (35 μL) to inactivate unreacted sites on the surface of the CM5 chips.

On the other hand, 35 mL (flow rate, 5 mL/min) of an equimolar mixture (final concentration 0.05 M) of N-ethyl-N-(dimethylaminopropyl) carbodiimide and N-hydroxysuccinimide (final concentration 0.05 M) was added, followed by treating with 1 M ethanolamine (35 μL) to prepare the control.

Next, the 6-SL PAMAM conjugates were diluted in HBS-EP buffer solution (0.01 M HEPES, 0.15 M NaCl, 3 mM EDTA, 0.005% surfactant P20, pH 7.4). Dilutions of various levels of the 6-SL PAMAM conjugates were added to the CM5 chips attached to the HA at a flow rate of 50 μL/min. Thereafter, HBS-EP buffer solution was added to the CM5 chips to promote dissociation. After 3 minutes, 2 M NaCl (50 μL) was added to the CM5 chips to regenerate the surface of the CM5 chips. The reaction results were analyzed using BIAcore 3000 (GE Healthcare, Uppsala, Sweden), operated using BIAcore 3000 control and BIAevaluation software (version 4.0.1), and then displayed as a function of time (sensorgram) at 25° C. (FIG. 3a).

As shown in FIG. 3a, it was confirmed that only some 6SL-PAMAM conjugates (S3-G4, S4-G4, S7-G5, and S8-G5) among the 6SL-PAMAM conjugates used showed a high binding affinity for HA proteins.

In particular, it was confirmed that the 6SL-PAMAM conjugates (S3-G4, S4-G4, and S7-G5), in which the distance between 6SL ligands was higher than or equal to 2.4 nm, all showed a high binding affinity for HA proteins.

However, the 6SL-PAMAM conjugates (S2-G3, S6-G4, S9-G5, and S10-G5), in which the distance between 6SL ligands was smaller than 1.9 nm, showed a remarkably low binding affinity for HA proteins. In addition, it was confirmed that most conjugates (S6-G4, S9-G5, and S10-G5) showed a remarkably low binding affinity for HA proteins despite containing more 6SL ligands compared to the 6SL-PAMAM conjugate (S3-G4, S4-G4, and S7-G5), in which the distance between 6SL ligands is greater than or equal to 2.4 nm.

On the other hand, it was confirmed from the result of analyzing the crystal of HA trimer that the distance between the 6SL binding sites present inside the trimeric HA was about 4 nm (FIG. 3b).

Accordingly, based on the results above, it was found that when the distance between 6SL ligands contained in the 6SL-PAMAM conjugates was 2.4 nm to 4.0 nm, it can be effectively bound to HA proteins.

Additionally, it was found that it is preferable for the 6SL-PAMAM conjugates to be in a form containing ethylenediamine core of G4 and G5, and that it is preferable for the 6SL-PAMAM conjugates to contain an appropriate level of 6SL ligands depending on the type of the ethylenediamine core.

Specifically, it was found that it is preferable for the 6SL-PAMAM conjugate containing G4 to contain about 20 to 30 6SL ligands, and that it is preferable for the 6SL-PAMAM conjugate containing G5 to contain about 30 to 40 6SL ligands.

The analysis contents above were schematized using S3-G4 and S6-G4 among the 6SL-PAMAM conjugates above (FIG. 3c).

As shown in FIG. 3c, since the distance between ligand biding sites present in HA proteins, which are the surface antigens of H1N1 virus, was similar to the distance (about 3.1 nm) between 6SL ligands contained in the S3-G4, the analysis of the S3-G4 showed that it strongly binds to HA proteins, the surface antigens of H1N1 virus. On the contrary, since the distance between ligand biding sites present in HA proteins, which are the surface antigens of H1N1 virus, was different from the distance between 6SL ligands contained in the S6-G4 (about 1.6 nm), it was determined from analysis that the S6-G4 must be bound weakly to HA proteins, the surface antigens of H1N1 virus.

Example 5

Electron Microscopic Analysis

Influenza virus (A/California/07/2009) was purified using a method known in the art.

Briefly, chicken egg follicular fluid infected by influenza virus (A/California/07/2009) was collected and centrifuged (3000 rpm, 10 minutes) to obtain a supernatant. The obtained supernatant was centrifuged at high speed (19,000× g, 2 hours) to obtain a precipitate. The obtained precipitate was suspended in 1 mL of THE buffer solution (50 mM Tris-HCl (pH 7.4), 100 mM NaCl, and 1 mM EDTA), and then centrifuged (36,000× g, 2 hours) under the condition of a three-step discontinuous sucrose gradient (TNE buffer solution (2 mL) containing 50%, 40%, and 30% sucrose), and thereby virus-containing fractions were obtained. The obtained fractions were suspended in PBS, and centrifuged (100,000× g, 1 hour, 4° C.) once more to obtain a precipitate. Thereafter, the precipitate was suspended in PBS (2 mL). The suspended virus-containing solution (20 μL) was mixed with 20 μL of S3-G4 solution (100 nmol/nL), and then the resultants were applied to Tecnai G2 spirit TEM (FEI company, Hillsboro, Oreg.), operated at an accelerating voltage of 120 kV, to carry out the transmission electron microscopy (TEM) analysis (FIG. 4). In particular, for the control, it was prepared by adding the virus-containing solution (5 μL) to a carbon-coated grid that had been glow-discharged for 3 minutes in the air, followed by staining the same using 2% uranyl acetate.

As shown in FIG. 4, S3-G4 particles (about 7 nm) with spherical shapes (top left panel) and bleb formation on the surface of H1N1 resulting from the binding of the S3-G4 (bottom right panel) were observed. However, the bleb formation was not observed when treated with G4 PAMAM dendrimers not having 6SL ligands (bottom left panel). It is expected that the bleb formation may result from the surface aggregation of S3-G4, and as a result, it was analyzed that viral attachment, intracellular entry, and endosomal fusion and escape will be inhibited.

Example 6

Analysis of Virus Infection Process

First, influenza virus (A/PR/8/34) was purified, and suspended in PBS (1 mL) to obtain virus-containing solution. A 100 μM R18 solution (6 μL) was added to the virus-containing solution, and allowed to react at room temperature for 1 hour to single-label the resultant with R18; or an ethanol solution (6 μL) containing DiOC18 (33 μM) and R18 (67 μM) was added to the virus-containing solution and the reaction mixture was reacted while gently shaking at room temperature for 1 hour to double-label the resultant with DiOC18 and R18. The solution after the reaction was filtered using 0.22 μm membrane filter (Millipore).

Next, MDCK cells were cultured at 37° C. for 24 hours in a 5% $CO_2$ condition. The filtered virus-containing solution was added to the cultured cells, and allowed to react at 4° C. for 20 minutes. After completion of the reaction, the liquid components were removed and the cells were washed 3 times with cold PBS. The cells were imaged using confocal microscopy (LSM700; Carl Zeiss) at 488 nm and 594 nm wavelengths at 37° C. in a 5% $CO_2$ condition (FIG. 5).

According to the results of the analysis using the virus which was single-labeled with R18 shown FIG. 5, it was confirmed that S3-G4 inhibited attachment of R18-labeled virus to the surface of MDCK cells.

Additionally, according to the results of the analysis using the virus which was double-labeled with DiOC18 and R18 shown in FIG. 5, the green and yellow viral particles were confirmed after treating with the both R18- and DiOC18-labeled control viruses, whereas no yellow and green viral particles were confirmed in the virus pretreated with S3-G4. Accordingly, it was found that S3-G4 was involved in the intracellular entry of the virus.

Example 7

Immunofluorescence Analysis

MDCK cells were seeded in 48-well plates, and infected with various H1N1 viruses (A/NWS/33, A/Puerto Rico/8/43 and A/California/07/2009) or H3N2 virus (A/Shandong/9/93) at 37° C. for 24 hours under the condition treated or untreated with S3-G4 (10 nmol/mL or 100 nmol/mL). The infected cells were treated with 4% paraformaldehyde, fixed at room temperature for 10 minutes, and washed with cold PBS. Thereafter, the resultants were reacted for 10 minutes by adding PBS containing 0.25% Triton X-100, and then washed again 3 times with PBS for 5 minutes each. The washed cells were treated with an influenza virus A NP-specific monoclonal antibody for 1 hour, and then reacted for another 1 hour by adding an Alexa 488-conjugated goat anti-mouse secondary antibody. Thereafter, the resultants were imaged using inverted fluorescent microscope (FIG. 6). Herein, nuclei of the cells were counterstained using NucBLue fixed cell stain (Life technologies), and actins of the cells were stained using ActinRed 555 ReadyProbes Reagent (Life technologies).

As shown in FIG. 6, it was confirmed that the expression level of the NP protein labeled in green was rapidly increased in MCDK cells (the control) infected by H1N1 virus. However, it was also confirmed that the expression level of the NP protein was low when treated with the S3-G4 conjugate.

Example 8

Analysis of 6SL-PAMAM Conjugate on Influenza Virus Infection Inhibition Under in Vivo Condition

Example 8-1

Production of Mice Infected With Influenza Virus

Female pathogen-free BALB/c mice (6 weeks) weighing 18 g to 20 g were used to analyze the ability of the 6SL-PAMAM conjugates for inhibiting influenza virus infection.

The mice were anesthetized by intraperitoneal injection of Avertin (375 mg/kg), and then S3-G4 was intranasally administered. After 10 minutes, the mice were infected by intranasal administration of H1N1 virus (A/NWS/33) in an amount of $10^4$ EID50 (50% egg infective dose). Herein, the mice were separated into 4 test groups according to the administration level of the S3-G4 and virus: positive control (administered with virus alone), negative control (administered with S3-G4 alone), comparative group (administered with PBS alone), and experimental group (administered with virus and S3-G4 (50 µmol/kg)). The mice in each test group were raised for 14 days, and then the experiments were carried out.

Example 8-2

Analysis of Virus Titer in Lung Tissue

After enucleating lungs from each mouse raised for 14 days, lysates thereof were obtained. Thereafter, the obtained lysates were centrifuged at 1400 g at 4° C. for 20 minutes to obtain supernatants. The supernatants were diluted 10-fold by adding PBS. The diluted supernatants were treated with MDCK cells, and then the virus titer contained in the supernatants were determined from the tissue culture infective dose ($TCID_{50}$) (FIG. 7a).

As shown in FIG. 7a, it was confirmed that the virus titer detected from the lung of the mice to which S3-G4 was administered exhibited a level 10 times lower than that of the control to which S3-G4 was not administered.

Example 8-3

Histopathological Analysis of Lung Tissue

After enucleating lungs from each mouse raised for 14 days, these were fixed with 10% formalin. Thereafter, tissue sections thereof were obtained, and then stained with hematoxylin and eosin. Histopathological examination thereon was carried out (FIG. 7b).

As shown in FIG. 7b, in the case of the positive control (H1N1), infiltration of inflammatory cells, such as monocytes and lymphocytes, was observed in the bronchiolar region located near the lung; alveolar wall thickening and moderate hemorrhaging were observed; and it was observed that lesions were diffuse throughout the entirety of the lobes. On the contrary, in the case of the experimental group (H1N1+S3–G4), it was observed that inflammatory lesions were reduced, and that infiltration of monocytes and lymphocytes in the bronchiolar and alveolar regions located near the lung was also reduced.

Example 8-4

Analysis of Cytokine Level in Lung Tissue

After enucleating lungs from each mouse raised for 14 days, levels of the cytokine (IL-6, IL-10, TNF-α, CXCL1, CXCL2, or CCL2) contained in the lysates were measured and compared (FIG. 7c).

As shown in FIG. 7c, it was confirmed that the levels of TNF-α, IL-10, CXCL1, and CXCL2 were not particularly different in the positive control (H1N1) and the experimental group (H1N1+S3–G4). However, the levels of IL-6 and CCL2 were significantly decreased in the experimental group (H1N1+S3–G4) compared to the positive control (H1N1).

Example 8-5

Analysis of Survival Rate of Mice

Changes in the survival rate of each mouse raised for 14 days were analyzed (FIG. 7d).

As shown in FIG. 7d, it was confirmed that the survival rate did not change in the negative control (S3-G4 (50 µmol/kg)) and the comparison group (PBS) even after the breeding period passed. However, in the case of the positive control (H1N1), the survival rate began to decrease from the $6^{th}$ day, and all mice were dead when 10 days had elapsed. On the contrary, in the case of the experimental group (H1N1+S3–G4), it was confirmed that the survival rate was decreased to about 75% on the $8^{th}$ day, but the survival rate did not change thereafter.

Example 8-6

Analysis of Body Weight Change in Mice

The survival rate of each mouse raised for 14 days was analyzed (FIG. 7e).

As shown in FIG. 7e, it was confirmed that the negative control (S3-G4 (50 µmol/kg)) and the comparison group (PBS) showed tendencies of gradually increasing the body weight as the breeding period elapsed. However, in the case of the positive control (H1N1), it was confirmed that the body weight of the mice decreased with the passage of the breeding period until the $9^{th}$ day, which was the day immediately before the death. On the contrary, in the experimental group (H1N1+S3–G4), it was confirmed that the body weight of the mice decreased with the elapse of the breeding period until the $9^{th}$ day, but the body weight was recovered thereafter even when the breeding period had elapsed.

Example 9

Effect of 6SL-PAMAM Conjugate on Antiviral Drug-Resistant Virus

Example 9-1

Immunofluorescence Analysis of Antiviral Drug-Resistant Virus

It has been reported that oseltamivir-resistant mutants emerge rapidly with the increasing use of commonly used NA-inhibiting antiviral drugs. Therefore, it was attempted to confirm whether S3-G4, a type of the 6SL-PAMAM conjugates provided in the present invention, could inhibit infection by oseltamivir-resistant H1N1 virus.

Briefly, infection inhibition by S3-G4 against oseltamivir-resistant H1N1 virus (A/Gyeongnam/1820/2009) isolated from a one-year-old female patient who died during hospitalization despite receiving oseltamivir and peramivir treatments was evaluated using immunofluorescence assay (FIG. 8a).

As shown in FIG. 8a, it was confirmed that S3-G4 (10 nmol/mL) inhibited oseltamivir-resistant H1N1 virus infection by 90%.

Example 9-2

Microneutralization Analysis on Antiviral Drug-Resistant Virus

The method of Example 3 was carried out, except that oseltamivir-resistant H1N1 virus (A/Gyeongnam/1820/2009) and S3-G4 were used for the virus and the 6SL-PAMAM conjugate, respectively. Thereafter, the infection inhibitory activity of S3-G4 against oseltamivir-resistant H1N1 virus (A/Gyeongnam/1820/2009) was analyzed (FIG. 8b).

As shown in FIG. 8b, it was confirmed that S3-G4 exhibited the activity of inhibiting infection against oseltamivir-resistant H1N1 virus (A/Gyeongnam/1820/2009; $IC_{50}$=5.8 μM), similar to the activity of S3-G4 observed against H1N1 virus (A/California/04/2009; $IC_{50}$=3.4 μM).

Example 9-3

Analysis of Plaque Reduction on Antiviral Drug-Resistant Virus

H1N1 virus (A/Gyeongnam/1820/2009), which had been treated or untreated with S3-G4, was added to MDCK cells, and the MDCK cells were infected for 1 hour. Thereafter, the infected MDCK cells were washed with PBS to remove the viruses that were not attached, and then treated with various concentrations of oseltamivir. In addition, the cells were cultured in agarose solid medium. The cultured solid medium was overlaid with overlay medium containing 1% agarose, and then cultured at 37° C. for 48 hours. After completion of the cultivation, the lower part of the solid medium was stained with 1% crystal violet, and the plaques were counted (FIG. 8c).

As shown in FIG. 8c, it was confirmed that the plaque formation was significantly decreased in the MDCK cells infected with oseltamivir-resistant H1N1 virus when oseltamivir and S3-G4 were co-administered, compared with the case of administering oseltamivir alone.

Based on the results above, it was confirmed that the 6SL-PAMAM conjugates of the present invention also exhibited an inhibitory activity against viruses that are resistant to antiviral drugs.

From the foregoing, one of ordinary skill in the art to which the present invention pertains will be able to understand that the present invention may be embodied in other specific forms without modifying the technical concepts or essential characteristics of the present invention. In this regard, the exemplary embodiments disclosed herein are only for illustrative purposes and should not be construed as limiting the scope of the present invention. On the contrary, the present invention is intended to cover not only the exemplary embodiments but also various alternatives, modifications, equivalents, and other embodiments that may be included within the spirit and scope of the present invention as defined by the appended claims.

The invention claimed is:

1. A conjugate comprising a core and ligands bound to the surface of the core, the core including polyamidoamine and each of the ligands being a sialic acid derivative, wherein:
   the core is a fourth-generation (G4) dendrimer and
      the ligands are arranged with spacing of 2.0 nm to 3.1 nm on the surface of the core, or
      20 to 31 of the ligands are bound to the surface of the core; or
   the core is a fifth-generation (G5) dendrimer and
      the ligands are arranged with spacing of 1.6 nm to 2.4 nm on the surface of the core, or
      37 to 56 of the ligands are bound to the surface of the core;
and the sialic acid derivative is sialyloligosaccharide or sialyllactose.

2. The conjugate of claim 1, wherein the core is a G4 dendrimer and the ligands are arranged with spacing of 2.0 nm to 3.1 nm on the surface of the core.

3. The conjugate of claim 1, wherein the core is a G4 dendrimer and the 20 to 31 ligands are bound to the surface of the core.

4. The conjugate of claim 1, wherein the core is a G5 dendrimer and the ligands are arranged with spacing of 1.6 nm to 2.4 nm on the surface of the core.

5. The conjugate of claim 1, wherein the core is a G5 dendrimer and the 37 to 56 ligands are bound to the surface of the core.

6. The conjugate of claim 1, wherein the core has a diameter of 4.5 nm.

7. The conjugate of claim 1, wherein the core has a diameter of 5.4 nm.

8. The conjugate of claim 1, wherein the sialic acid derivative is selected from the group consisting of 3'-sialyllactose, 6'-sialyllactose, sialyl lacto-N-tetraose, disialyl lacto-N-tetraose, and combinations thereof.

9. The conjugate of claim 1, wherein each of the ligands is bound to the surface of the core via a reactive group of the core or via a linker.

10. A pharmaceutical composition for preventing or treating influenza virus infection, comprising the conjugate of claim 1 and a pharmaceutically acceptable carrier.

11. A food composition for preventing or improving influenza virus infection, comprising the conjugate of claim 1 and a food material.

12. A method of preventing or treating influenza virus infection, comprising the step of administering the conjugate of claim 1 to a subject who is suspected of being infected with influenza virus or is infected with influenza virus.

13. The method of claim 12, wherein the influenza virus is influenza A virus or influenza B virus.

14. The method of claim 12, wherein the conjugate binds with hemagglutinin (HA) of influenza virus to inhibit infection of the virus.

15. A method of inhibiting influenza virus infection, comprising the step of treating influenza virus with a conjugate of claim 1.

* * * * *